US009341617B2

(12) United States Patent
Mautner et al.

(10) Patent No.: US 9,341,617 B2
(45) Date of Patent: May 17, 2016

(54) METHOD OF IDENTIFYING CD4+ T CELL ANTIGENS

(75) Inventors: Josef Mautner, Munich (DE); Uta Behrends, Munich (DE); Slavoljub Milosevic, Munich (DE)

(73) Assignee: Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 1409 days.

(21) Appl. No.: 11/918,978

(22) PCT Filed: Apr. 24, 2006

(86) PCT No.: PCT/EP2006/003759
§ 371 (c)(1),
(2), (4) Date: Apr. 2, 2009

(87) PCT Pub. No.: WO2006/111423
PCT Pub. Date: Oct. 26, 2006

(65) Prior Publication Data
US 2009/0298056 A1    Dec. 3, 2009

(30) Foreign Application Priority Data

Apr. 22, 2005  (EP) .................................... 05008924

(51) Int. Cl.
*C12N 5/00* (2006.01)
*C12N 5/02* (2006.01)
*G01N 33/53* (2006.01)
*G01N 33/50* (2006.01)

(52) U.S. Cl.
CPC .... *G01N 33/505* (2013.01); *G01N 2333/70514* (2013.01)

(58) Field of Classification Search
None
See application file for complete search history.

(56) References Cited

FOREIGN PATENT DOCUMENTS

WO    WO 02/088740    11/2002

OTHER PUBLICATIONS

Davis et al., 1997, PNAS, VOl. 94: 2128-32.*
CHen et al., 2004, J. Clin. Invest. vol. 113, 1754-1762.*
Mandell et al., 2002, Lab. Invest. vol. 82: 1631-1636.*
Corput et al., Published online Nov. 2004, Leukemia, vol. 19: 279-285.*
Henics et al., 2003. Biotech. vol. 35: pp. 196-200, 202, 204, 206, and 208.*
Kashanchi et al., 1989, PNAS. vol. 86: 2157-61.*
Koelle, 2003, Methods, vol. 29: 213-226.*
Zacchi et al., 2003, Genomre Res.Vo. 13: 980-990.*
Sieber et al., 2001, Nat. Biotech. vol. 19: 456-460.*
Neophytou et al., 1996, PNAS, vol. 93: 2014-2018.*
International Search Report and Written Opinion of the International Searching Authority for International Application No. PCT/EP2006/003759 (Oct. 31, 2006).
Communication pursuant to R.44 or R.45 EPC corresponding to European Application No. 05008924.2-2404 dated Feb. 6, 2006.
Alderson et al., "Expression Cloning of an Immunodominant Family of Mycobacterium tuberculosis Antigens Using Human CD4+ T Cells," J. Exp. Med., The Rockefeller University Press, vol. 191, No. 3, pp. 551-559 (Feb. 7, 2000).
Sanderson et al., "Identification of a CD4+ T Cell-stimulating Antigen of Pathogenic bacteria by Expression Cloning", J. Exp. Med., The Rockefeller University Press, vol. 182 (Dec. 1995).
Gladow e al., "MLV-10A1 Retrovirus Pseudotype Efficiently Transduces Primary Human CD4+ T Lymphocytes", The Journal of Gene Medicine, vol. 2, pp. 409-415 (2000).
Behrends et al., "Novel products of the HUD, HUC, NNP-I and alpha-internexin genes identified by autologous antibody screening of a pediatric neuroblastoma library," Int. J. Cancer, vol. 100, pp. 669-677 (2002).
Davis et al., "Recombinant NY-ESO-1 protein with ISCOMATRIX adjuvant induces broad integrated antibody and CD4(+) and CD8(+) T cell responses in humans," Proc. Natl. Acad. Sci. USA, vol. 101, pp. 10697-10702 (2004).
Gorgievski-Hrisoho et al., "Serodiagnosis of infectious mononucleosis by using recombinant Epstein-Barr virus antigens and enzyme-linked immunosorbent assay technology," J. Clin. Microbiol., vol. 28, pp. 2305-2311 (1990).
Halder et al.,"Isolation of novel HLA-DR restricted potential tumor-associated antigens from the melanoma cell line FM3," Cancer Res., vol. 57, pp. 3238-3244 (1997).
Hamanaka et al., "Circulating anti-MUCI IgG antibodies as a favorable prognostic factor for pancreatic cancer," Int. J. Cancer, vol. 103, pp. 97-100 (2003).
Jager et al., "Monitoring CD8 T cell responses to NY-ESO-1: correlation of humoral and cellular immune responses," Proc. Natl. Acad. Sci. USA, vol. 97, pp. 4760-4765 (2000).
Kalams et al., "The critical need for CD4 help in maintaining effective cytotoxic T lymphocyte responses," J. Exp. Med., vol. 188, pp. 2199-2204 (1998).
McShane and Longnecker, "Cell-surface expression of a mutated Epstein-Barr virus glycoprotein B allows fusion independent of other viral proteins," Proc. Natl. Acad. Sci. USA, vol. 101, pp. 17474-17479 (2004).
Moosmann et al., "B cells immortalized by a mini-Epstein-Barr virus encoding a foreign antigen efficiently reactive specific cytotoxic T cells," Blood, vol. 100, pp. 1755-1764 (2002).

(Continued)

*Primary Examiner* — Amy Juedes
(74) *Attorney, Agent, or Firm* — Clark & Elbing LLP

(57) ABSTRACT

The present invention is directed to a method of identifying CD4+ T cell antigens as well as to antigens which were identified by such a method. The present invention further is directed to the application of those identified antigens in medicine.

22 Claims, 15 Drawing Sheets

(56) References Cited

OTHER PUBLICATIONS

Figure 1:
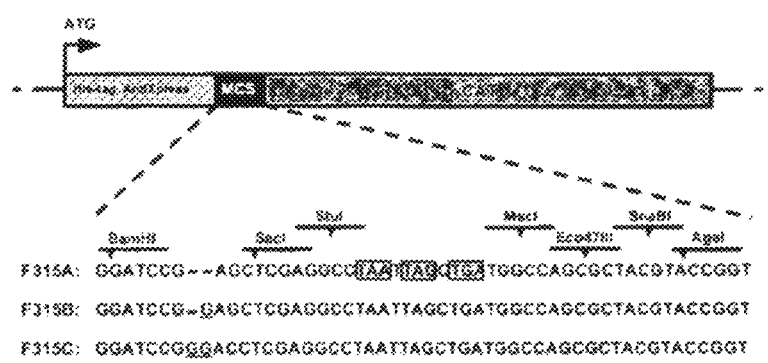
Figure 1:
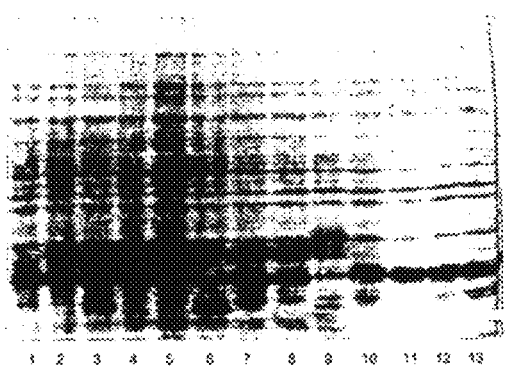

Neuhierl et al., "Glycoprotein gp110 of Epstein-Barr virus determines viral tropism and efficiency of infection," Proc. Natl. Acad. Sci. USA, vol. 99, pp. 15036-15041 (2002).

Pieper et al., "Biochemical identification of a mutated human melanoma antigen recognized by CD4(+) T cells," J. Exp. Med., vol. 189, pp. 757-766 (1999).

Sahara and Shastri, "Second class minors: molecular identification of the autosomal H46 histocompatibility locus as a peptide presented by major histocompatibility complex class II molecules," J. Exp. Med., vol. 197, pp. 375-385 (2003).

Sanderson et al., "Expression of endogenous peptide-major histocompatibility complex class II complexes derived from invariant chain-antigen fusion proteins," Proc. Natl. Acad. Sci. USA, vol. 92, pp. 7217-7221 (1995).

van Bergen et al., "Efficient loading of HLA-DR with a T helper epitope by genetic exchange of CLIP," Proc. Natl. Acad. Sci. USA, vol. 94, pp. 7499-7502 (1997).

Wang et al., "Identification of a novel major histocompatibility complex class II-restricted tumor antigen resulting from a chromosomal rearrangement recognized by CD4(+) Tcells," J. Exp. Med., vol. 189, pp. 1659-1668 (1999).

Wong et al., "Detection of diverse hepatitis C virus (HCV)-specific cytotoxic T lymphocytes in peripheral blood of infected persons by screening for responses to all translated proteins of HCV," J. Virol., vol. 75, pp. 1229-1235 (2001).

Zeng et al., "Generation of NY-ESO-I-specific CD4+ and CD8+ T cells by a single peptide with dual MHC class I and class II specificities: a new strategy for vaccine design," Cancer Res, vol. 62, pp. 3630-3635 (2002).

Aarnoudse et al., "Interleukin-2-Induced, Melanoma-Specific T Cells Recognize Camel, an Unexpected Translation Product of Lage-1," Int. J. Cancer: 82, 442-448 (1999).

Adhikary et al., "Control of Epstein-Barr virus infection in vitro by T helper cells specific for virion glycoproteins," The Journal of Experimental Medicine, vol. 203, No. 4, pp. 995-1006 (Apr. 17, 2006).

De Plaen et al., "Identification of genes coding for tumor antigens recognized by cytolytic T lymphocytes," Methods, vol. 12, pp. 125-142 (1997).

Fujii et al., "The CLIP-substituted invariant chain efficiently targets an antigenic peptide to HLA class II pathway in L cells," Hum. Immunol., vol. 59, pp. 607-614 (1998).

Horst et al., "A method for cDNA cloning in COS cells irrespective of subcellular site of expression," Nucleic Acids Res., vol. 19, pp. 45-56 (1991).

Kieff et al., "Epstein-Barr virus and its replication," In: B.N. Fields, D.M. Knipe and P.M. Howley (eds.), Fields Virology, Lippincott-Raven, Philadelphia, pp. 2511-2573 (2001).

Kortt et al., "Dimeric and trimeric antibodies: high avidity scFvs for cancer targeting," Biomol. Eng., vol. 18, pp. 95-108 (2001).

Lemmel et al., "The use of HPLC-MS in T-cell epitope identification," Methods, vol. 29, pp. 248-259, (2003).

Mautner et al., "Epstein-Barr virus nuclear antigen 1 evades direct immune recognition by CD4+ T helper cells," Eur. J. Immunol., vol. 34, pp. 2500-2509 (2004).

Monach et al., "A unique tumor antigen produced by a single amino acid substitution," Immunity, vol. 2, pp. 45-59 (1995).

Nimmerjahn, "Efficient generation and expansion of antigen-specific CD4+ T cells by recombinant influenza viruses," Eur. J. Immunol., vol. 33, pp. 3331-3341 (2003).

Romero et al., "Monitoring tumor antigen specific T-cell responses in cancer patients and phase I clinical trials of peptide-based vaccination," Cancer Immunol. Immunother., vol. 53, pp. 249-255 (2004).

Speiser et al., "Evaluation of melanoma vaccines with molecularly defined antigens by ex vivo monitoring of tumor-specific T cells," Semin. Cancer Biol., vol. 13, pp. 461-472 (2003).

Wang et al., "Cloning genes encoding MHC class II-restricted antigens: mutated CDC27 as a tumor antigen," Science, vol. 284, pp. 1351-1354 (1991).

\* cited by examiner

A

B

Coomassie® staining

Western Blot

A

B

A

B

SEQUENCE LISTING

```
<160> NUMBER OF SEQ ID NOS: 15

<210> SEQ ID NO 1
<211> LENGTH: 15
<212> TYPE: PRT
<213> ORGANISM: Artificial sequence
<220> FEATURE:
<223> OTHER INFORMATION: Artificially synthesized core epitope

<400> SEQUENCE: 1

Asp Asn Glu Ile Phe Leu Thr Lys Lys Met Thr Glu Val Cys Gln
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Artificially synthesized core epitope

<400> SEQUENCE: 2

Thr Asp Ala Trp Arg Phe Ala Met Asn Tyr Pro Arg Asn Pro Thr
1               5                   10                  15

<210> SEQ ID NO 3
<211> LENGTH: 47
<212> TYPE: DNA
<213> ORGANISM: Artificial sequence
<220> FEATURE:
```

```
<223> OTHER INFORMATION: Artificially synthesized oligonucleotide primer

<400> SEQUENCE: 3
gatccgagct cgaggcctaa ttagctgatg gccagcgcta cgtaccg              47

<210> SEQ ID NO 4
<211> LENGTH: 47
<212> TYPE: DNA
<213> ORGANISM: Artificial sequence
<220> FEATURE:
<223> OTHER INFORMATION: Artificially synthesized oligonucleotide primer

<400> SEQUENCE: 4
gatccggtac gtagcgctgg ccatcagcta attaggcctc gagctcg              47

<210> SEQ ID NO 5
<211> LENGTH: 15
<212> TYPE: PRT
<213> ORGANISM: Artificial sequence
<220> FEATURE:
<223> OTHER INFORMATION: Artificially synthesized epitope

<400> SEQUENCE: 5

Leu Glu Asn Leu Gln Ala Tyr Gln Lys Arg Met Gly Val Gln Leu
 1               5                  10                  15

<210> SEQ ID NO 6
<211> LENGTH: 21
<212> TYPE: DNA
<213> ORGANISM: Artificial sequence
<220> FEATURE:
<223> OTHER INFORMATION: Artificially synthesized forward primer

<400> SEQUENCE: 6
gaggtatata ttaatgtatc g                                          21

<210> SEQ ID NO 7
<211> LENGTH: 15
<212> TYPE: PRT
<213> ORGANISM: Artificial sequence
<220> FEATURE:
<223> OTHER INFORMATION: Artificially synthesized epitope

<400> SEQUENCE: 7

Phe Gly Gln Leu Thr Pro His Thr Lys Ala Val Tyr Gln Pro Arg
 1               5                  10                  15

<210> SEQ ID NO 8
<211> LENGTH: 35
<212> TYPE: DNA
<213> ORGANISM: Artificial sequence
<220> FEATURE:
<223> OTHER INFORMATION: Artificially synthesized oligonucleotide primer

<400> SEQUENCE: 8
tcgaggccta attagctgat ggccagcgct acgta                           35

<210> SEQ ID NO 9
<211> LENGTH: 35
<212> TYPE: DNA
<213> ORGANISM: Artificial sequence
<220> FEATURE:
<223> OTHER INFORMATION: Artificially synthesized oligonucleotide primer

<400> SEQUENCE: 9
ccggtacgta gcgctggcca tcagctaatt aggcc                           35
```

<210> SEQ ID NO 10
<211> LENGTH: 43
<212> TYPE: DNA
<213> ORGANISM: Artificial sequence
<220> FEATURE:
<223> OTHER INFORMATION: Artificially synthesized oligonucleotide primer

<400> SEQUENCE: 10
ccggtggcgg cgggagcggg ggcggggca gcggggcgg ggg         43

<210> SEQ ID NO 11
<211> LENGTH: 43
<212> TYPE: DNA
<213> ORGANISM: Artificial sequence
<220> FEATURE:
<223> OTHER INFORMATION: Artificially synthesized oligonucleotide primer

<400> SEQUENCE: 11 catgccccccg ccccgctgc ccccgccccc gctcccgccg cca         43

<210> SEQ ID NO 12
<211> LENGTH: 15
<212> TYPE: PRT
<213> ORGANISM: Artificial sequence
<220> FEATURE:
<223> OTHER INFORMATION: Artificially synthesized epitope

<400> SEQUENCE: 12

Arg Gln Ala Ile Arg Asp Arg Arg Asn Pro Ala Ser Arg Arg
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: Artificially synthesized epitope

<400> SEQUENCE: 13

Phe Gly Gln Leu Thr Pro His Thr Lys Ala Val Tyr Gln Pro Arg
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Artificially synthesized epitope

<400> SEQUENCE: 14

Leu Glu Asn Leu Gln Ala Tyr Gln Lys Arg Met Gly Val Gln Leu
1               5                   10                  15

<210> SEQ ID NO 15
<211> LENGTH: 21
<212> TYPE: DNA
<213> ORGANISM: Artificial sequence
<220> FEATURE:
<223> OTHER INFORMATION: Artificially synthesized forward primer

<400> SEQUENCE: 15
gaggtatata ttaatgtatc g         21

METHOD OF IDENTIFYING CD4+ T CELL ANTIGENS

CROSS-REFERENCE TO RELATED APPLICATIONS

This application is a continuation of PCT International Patent Application No. PCT/EP2006/003759, filed Apr. 24, 2006, which claims priority to European Patent Application No. 05008924.2, filed Apr. 22, 2005, the disclosures of each of which are incorporated herein by reference in their entirety.

The present invention is directed to a method of identifying CD4+ T cell antigens as well as to antigens which were identified by such a method. The present invention further is directed to the application of those identified antigens in the field of medicine.

CD4+ T cells (TC) play a central role in the orchestration of adaptive immune responses. By providing help in the form of secreted cytokines or cell surface signals, TC initiate and control antigen-specific humoral and cellular effector functions and sustain immunological memory. Thus, the identification of antigens recognized by TC is essential for understanding and modulating adaptive immune responses. TC recognize peptide/MHC II complexes on the surface of professional antigen presenting cells (pAPC), e.g. macrophages, B cells and dendritic cells (DC). The peptides presented on MHC class II molecules are mostly derived from exogenous or cell membrane proteins processed in the endosomal/lysosomal compartment.

There are two classes of MHC molecules, class I and class II, which are functionally distinguished by the type of antigen they bind and the subset of T cells with which they interact. The dichotomy between class I and class II molecules relates to their different roles in T cell activation. Class I molecules present peptides to MHC-class I-restricted CD8 positive cytotoxic T lymphocytes (CTL). These cells directly lyse target cells. Since class I molecules are expressed by nearly all nucleated cells, CTL are able to recognize and destroy virtually any cell if it presents the appropriate MHC/peptide complex. On the other hand, class II molecules present peptides to CD4+ T cells, the primary function of which is to secrete cytokines and to express cell surface molecules that promote activities of other lymphocytes, including B cells, macrophages and CTL. They play a dominant role in orchestrating an immune response.

It was desired for a long time to identify those antigens which could lead to an activation of TC in order to promote or to avoid immune responses.

In the past, different methods for the identification of antigens recognized by TC have been developed. Two tumor antigens recognized by melanoma-specific TC have been identified through biochemical purification of antigenic proteins from tumor lysates combined with mass spectrometric sequencing (Monach et al., 1995; Pieper et al., 1999). In this approach, protein fractions obtained by biochemical separation methods are added to cultures of APC, which take-up, process and present these exogenous antigens on MHC class II, where they can be recognized by antigen-specific TC. Positive fractions are further separated, and ultimately the antigen recognized by the TC is identified by mass spectroscopy within highly purified positive fractions. Because proteins differ in their biochemical behaviour, the purification procedure has to be tailored for each antigen. Furthermore, the highly sophisticated technical equipment required for antigen identification precludes a broader application of this approach.

Attempts to isolate antigenic peptides directly from MHC class II molecules as applied for the identification of peptides recognized by TC by mass spectrometric sequence analysis has been unsuccessful in most cases for peptides recognized by TC. In contrast to MHC class I molecules, the peptide binding groove of class II molecules has open ends and accommodates peptides heterogeneous in length. However, a peptide derived from gp100 was identified using this approach (Halder et al., 1997).

Several melanoma-specific TC antigens have been identified by a modified cDNA expression cloning approach originally developed to identify MHC class I-restricted tumor antigens (De Plaen et al., 1997; Wang et al., 1999a; Wang et al., 1999b). To overcome the differences in antigen presentation, the cDNAs were fused to the invariant chain gene. Signal sequences within the first 80 amino acids of invariant chain direct the resulting fusion proteins into the endosomal/lysosomal compartment where processing and loading onto MHC class II molecules occurs (Fujii et al., 1998; Sanderson et al., 1995; van Bergen et al., 1997). As recipient cell line for the expression of cDNA libraries, highly transfectable HEK293 cells were genetically modified to become artificial pAPC. The cells were stably transfected with cDNAs encoding HLA-D$\alpha$ and -D$\beta$, which form the appropriate MHC class II restriction element, HLA-DM$\alpha$ and -DM$\beta$, which facilitate binding of peptides to MHC class II molecules, and invariant chain, which directs newly synthesized MHC class II molecules into the MHC class II processing and loading compartment (Wang et al., 1999b). This method is dependent on knowledge of the restricting MHC molecule and requires stable transfection of HEK293 cells with five different genes.

The most recent methodology developed for the identification of TC antigens is by bacterial expression cloning. A $\lambda$-phages expression library established from genomic DNA of *Mycobacterium tuberculosis* was used by Alderson et al. for the identification of antigens recognized by TC specific for this human pathogen (Alderson et al., 2000). Dendritic cells (DC) or macrophages were incubated with *E. coli* infected with $\lambda$-phages expressing mycobacterial antigens. Following phagocytosis of whole bacteria, peptides derived from bacterially expressed proteins are presented on MHC class II molecules. By probing these APCs with TC, single bacteria expressing the antigens were identified.

A similar strategy was recently applied to define the antigen recognized by minor histocompatibility (in HA) antigen-specific TC (Sahara and Shastri, 2003). Instead of $\lambda$-phages, a cDNA plasmid library was expressed in *E. coli* and pools of transformed bacteria were fed to DC. Using a model antigen, feasibility and sensitivity of this approach was recently verified with human EBV-transformed lymphoblastoid cell lines (LCL) as APC and complement opsonized bacteria, resulting in the detection of the model antigen within pools of 300 bacteria expressing irrelevant proteins (van de Corput et al., 2005). However, only a small proportion of eukaryotic genes are expressed at sufficiently high levels in bacteria to allow for such large pool sizes. Because most of the proteins are expressed at significantly lower levels, many antigens will remain undetected with this approach.

Therefore, it is a problem underlying the present invention to provide an improved method for identifying T helper cell antigens. It is a further object of the invention to identify and provide heretofore unknown T helper cell antigens. Additionally, it is a problem underlying the present invention to provide a method for the early diagnosis/prognosis of several diseases.

These problems are solved by the subject-matter of the independent claims. Preferred embodiments are set forth in the dependent claims.

In summary, the present invention brings about the following advantages and results:

The inventors developed a simple and reliable procedure for mapping epitopes within antigens and for the identification of same. A simple and fast bacterial cDNA expression cloning approach is disclosed that allows rapid identification of T helper cell antigens. Short antigenic fragments created by digestion with frequently cutting restriction enzymes are randomly ligated to the coding sequence of a marker gene, for example and preferably chloramphenicol acetyltransferase (CAT) in a bacterial expression vector. Bacteria expressing antigen-CAT fusion proteins are then fed directly to MHC class II$^+$ antigen presenting cells and probed with antigen-specific TC. Bacterial colonies recognized by TC are expanded, and the antigenic fragments identified by plasmid extraction and sequence analysis. Using this approach, two antigens recognized by Epstein-Barr virus (EBV) specific TC were identified as an example. The simplicity and high sensitivity of this method facilitates the identification of antigens within complex cDNA libraries.

The present invention in particular is directed to the following aspects and embodiments:

According to a first aspect, the present invention provides a method of identifying TC antigens comprising the steps of:
a) providing an antigen encoding nucleic acid from antigen expressing cells or tissue and obtaining antigenic fragments of said nucleic acid;
b) expressing one or more of said fragments as a fusion protein comprising said fragment and a marker in a suitable host cell;
c) contacting said fusion protein expressing cell with antigen presenting cells (APC's) and co-cultivating with antigen-specific TC; and
d) determining, whether the TC are activated by said fusion protein expressing cells.

The major drawbacks of the prior art methods of identifying TC antigens are overcome by the present approach. As mentioned above, it is already known to express potentially antigenic proteins, for example of human origin, in bacterial cells followed by incubation with MHC II positive APC's. However, a drawback which is involved in this method is the strongly varying expression level of those potential antigens in bacterial cells. Many eukaryotic proteins are toxic to *E. coli*, resulting in low or undetectable levels of expression. In addition, large proteins (>100 kDa) are poorly expressed in bacteria.

In contrast thereto, the present method has the advantage to provide a high and uniform expression of the antigens in host cells, for example bacterial cells. By the fragmentation provided herein, it is further possible to analyze antigens, which as a whole would be toxic for the host cell.

It is noted that generally one single potential antigenic fragment is expressed in the fusion protein in step b). However, it is also feasible to include two or more, for example three, shorter fragments into the fusion protein coding nucleic acid.

Generally, the term "nucleic acid" as used herein encompasses both RNA and DNA, including cDNA, genomic DNA, and synthetic (e.g., chemically synthesized) DNA.

According to a preferred embodiment, the fragments are obtained by cleaving the antigen encoding nucleic acid with one or more frequently cutting restriction enzymes, which are preferably selected from the group consisting of AciI, MnlI, BsaJI, and CviJI.

It is noted that preferably enzymes are used which recognize a DNA recognition sequence of four or less bases. For example, for enzyme AciI the recognition sequence is CCGC, for MnlI CCTC. Even shorter recognition sequences are RGCY for CviJI.

It is, however, also possible to produce short DNA fragments by other biological, chemical or physical methods, including partial digestion by nucleases (e.g. DNAseI) or sonification.

According to a preferred embodiment, the fragments have a size ranging from about 25 to about 300 bp, preferably from 40 to 200 bp and are most preferably about 90 bp. Or in other words, the antigenic protein fragments vary in size from about 9 to about 100 amino acids. Shorter fragments will not work properly, since peptides need a length of a least 9 aa for binding to MHC II molecules. Fragments of more than 300 bp are not included in the invention, because fragments bigger than 300 bp are usually expressed at much lower levels and/or impair the marker (for example CAT) function.

A more preferred range is from 40 to 200 bp. About 90 bp is most preferred.

The host cell for expressing the fusion protein preferably is selected from prokaryotic and lower eukaryotic cells, preferably yeast cells and bacterial cells. Preferred bacterial cells are *E. coli* and *B. subtilis*.

In a preferred embodiment, the fragments are expressed as a fusion protein by introducing an expression vector, preferably a plasmid, containing the nucleic acid sequence coding for the fragment and a marker, into the host cell.

The expression vector preferably comprises one or more regulatory sequences. The term "expression vector" generally refers to a plasmid or phage or virus or vector, for expressing a polypeptide from a DNA (RNA) sequence. An expression vector can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell.

The expression vector may contain further "functional" sequences, depending from the detection methods used in the present method. For example, the expression vector may comprise an antibody recognition sequence for subsequent Western Blotting and/or a His-Tag.

In a in particular preferred embodiment the marker gene is selected from antibiotic resistance genes, preferably chloramphenicol acetyltransferase (CAT) or from fluorescent marker genes, preferably coding for green or red fluorescent protein, or LacZ.

For example, the bacterial colonies expressing LacZ fusion product might be identified via XGal staining.

Furthermore, the present invention encompasses all marker genes which produce gene products essential for growth of mutant bacteria (which do not express the gene product).

The fusion of antigenic fragments to CAT offers several advantages. First, chloramphenicol treatment allows selection of bacteria expressing antigen-CAT fusion proteins in frame, which greatly reduces the number of colonies to screen. Second, antigenic fragments fused to CAT are expressed at high level, even when derived from proteins toxic to bacteria. Third, the uniformly high expression level of antigen-CAT fusion proteins allows to establish large and representative pool sizes.

The nucleic acid coding for the antigen preferably is cDNA obtained by transcribing mRNA isolated from the antigen-expressing cells or tissue into cDNA.

In step c) the APCs are preferably selected from dendritic cells, macrophages and lymphocytes, preferably from a lymphoblastoid cell line (LCL).

Following step d) the method of the invention may additionally comprise expanding fusion protein expressing host cells which activate antigen specific TC and identifying the antigenic fragments contained therein by sequence analysis.

The activation of said TC preferably is measured by determining cytokine secretion or proliferation. This preferably is accomplished by cytokine-ELISA. However, there are also further methods for measuring at hand, for example detecting GFP in TC following activation (GFP encoded by a reporter gene construct were introduced into said TC before).

Generally, the antigen is derived from pathogens including bacteria and viruses, or from cDNA libraries. However, further sources for antigenic proteins may include all kind of tissues, in particular human tissues, preferably tumor explants in the case of tumor patients or inflamed tissues in cases of autoimmunity or infection.

According to a further embodiment the antigen-specific TC are isolated by in vitro stimulation of autologous stimulator cells. TC are isolated from peripheral blood, secondary lymphoid organs (e.g. lymph node) or tissue of patients (e.g. tumor explants in the case of tumor patients or inflamed tissues in cases of autoimmunity or infection). The TC are repeatedly stimulated in vitro using appropriate antigen presenting cells (e.g. tumor cells) until TC lines with selective reactivity against the target tissue are obtained.

In a second aspect, the present invention provides a TC antigen, which was identified by the method as disclosed above.

The identification of TC antigens forms the basis for various scientific and clinical applications. Given the central role of TC in adaptive immune responses, elucidation and characterization of antigen-specific immune responses is dependent on the identification of TC antigens.

Furthermore, the TC antigens provide valuable diagnostic and prognostic markers. For example, TC controlled humoral immune responses against certain antigens only occur in cancer patients and often long before tumor detection by current diagnostic methods (Behrends et al., 2002). Likewise, immune responses against MUC1 have been identified as a favorable prognostic marker in patients with pancreatic cancer (Hamanaka et al., 2003).

Moreover, the definition of TC antigens is mandatory for modulating antigen-specific immune responses, including active and passive immunizations, as well as other forms of immunotherapy.

In a third aspect, the invention is directed to a method for selecting heteroclitic variants of the identified antigens. By expressing and testing mutants of the identified antigens as fusion proteins, those variants can be identified that cause stronger or weaker T cell responses. For example, exchange of the amino acids that are responsible for MHC binding may lead to peptide variants that bind with higher affinity and thereby induce stronger T cell responses, e.g. in vaccination experiments. On the contrary, exchange of amino acids that interact with the T cell receptor may lead to antigenic peptides that no longer activate the T cell but induce anergy instead. Such antigen variants are helpful in dampening unwanted immune responses, for example in autoimmune diseases. The third aspect thus provides a method for selecting TC antigen variants comprising the steps of identifying a TC antigen by a method as defined above and selecting antigen variants with improved or diminished T cell stimulatory capacity compared to said antigen.

According to a fourth aspect, the invention provides a method for detecting a disease in a patient, preferably a human patient, comprising the steps of:
a) providing TC from said patient;
b) contacting a disease specific antigen as defined hereinabove with said TC; and
c) detecting, whether the TC are specific for said disease specific antigen.

The detection in step c) may be performed by techniques well known in the art, for example by FACS or ELISPOT assay.

This detection method can be used for the early detection and/or prognosis of several diseases, in particular cancer or autoimmunity diseases. For example, in the case of the early detection of cancer, TC are derived from a patient (for example by taking a blood sample from said patient), the TC are isolated and contacted with an antigen, which has been proven by the method of the present invention to be a cancer specific and TC specific antigen. A positive reaction will indicate that the patient is suffering from cancer.

The materials, methods, and examples which follow are illustrative only and not intended to be limiting.

The invention is now further illustrated by the accompanying drawings, in which the following is shown:

FIG. 1

(A) Schematic depiction of the expression vector. The expression plasmids F315A, B and C are derivatives of the bacterial expression plasmid pTrcHisA (Invitrogen), which contains an IPTG-inducible promoter and translational start site (ATG) for the expression of N-terminally His- and antibody (AntiXpress) epitope-tagged fusion proteins. Into this plasmid, the coding sequence of the chloramphenicol acetyltransferase (CAT) was inserted together with a multiple cloning site (MCS). This MCS contains unique recognition sequences for several restriction enzymes that allow insertion of blunt end antigenic fragments or sticky end DNA linkers. The StuI and the MscI sites are separated by stop codon in all three reading frames (shaded boxes) to prevent CAT expression from non-recombinant plasmids. The plasmids F315A, B and C differ by one or two nucleotides inserted in front of the multiple cloning site only. (B) Fusion proteins are highly expressed in bacteria. To assess protein expression from these plasmids, short antigenic fragments were randomly inserted into the MCS. Following transformation, bacteria were plated on agar plates containing chloramphenicol, and thirteen bacterial colonies further examined. Bacterial extracts were separated by SDS-PAGE and analysed by Coomassie® staining and Western blot using the AntiXpress antibody. Translation of the protein expressed by colony #6 is initiated at an ATG within the cDNA fragment, giving rise to an antigen-CAT fusion protein that lacks the His-tag and the antibody epitope.

FIG. 2

Antigen Presentation Experiments Using Liquid Cultures of Transformed Bacteria and Purified Proteins.

Bacteria transformed either with the plasmid F216 encoding the epitope recognized by the influenza M1-specific T cell clone M1-E5, or with a plasmid encoding an irrelevant epitope were grown as liquid cultures and protein expression induced by addition of IPTG when the cultures reached an $OD_{600}$ of 0.8. The bacteria were harvested four hours later by centrifugation, and resuspended to an $OD_{600}$ of 5. Different ratios of bacteria transformed with plasmid F216 and bacteria transformed with a control plasmid encoding an irrelevant fusion protein were added to $1 \times 10^5$ autologous LCL in 200 µl of LCL media supplemented with 100 µg/ml gentamicin to terminate bacterial growth. In parallel, purified F216 fusion protein (500 µg/ml) and control protein (500 µg/ml) were mixed at the indicated ratios and added to LCL. After 24 hours of incubation, $1 \times 10^5$ CD4+ T cells were added and cytokine secretion by the T cells determined 20 hours later by ELISA. The T cells specifically recognized target cells incubated with whole bacteria or purified protein with similar efficiency over a broad concentration range.

FIG. 3

Identification of the T Cell Epitopes within Known Antigens.

The coding sequences of the EBV antigens BALF4 and BRLF1 were cleaved with frequently cutting restriction enzymes and the fragments ligated into the expression vector. Following transformation, bacteria were cultured in 96 well plates at 14 cfu/w in the case of BALF4 and at 60 cfu/w for BRLF1. After overnight incubation, 100 µl from each well were transferred to 1.5 ml of superbroth media in a 96 deep well block and the rest frozen as mother plate in 20% glycerol. Bacteria were harvested by centrifugation when the optical density reached an $OD_{600}$ of 1, and resuspended in 300 µl of media. From each well, 10 µl were added to APC and co-cultured for 20 hours before addition of T cells. After 24 hours, GM-CSF secretion by the T cells was measured by ELISA. (A) BALF4 B5 T cells recognized five pools of which pool D1 was further analysed. Bacteria from this pool were plated on agar plates. Of the 36 single colonies tested 16 were recognized by the T cells. Sequence analysis of the plasmids showed that all expressed the same 27 aa peptide derived from BALF4 fused in frame with CAT. The epitope, marked as boxed sequence, was verified using synthetic oligos partially spanning the identified region. The BRLF1 library was tested the same way using clones 3A10 (B) and 1H3 (C). The single colony recognized by clone 3A10 contained an insert coding for a peptide of 27aa derived from BRLF1. The epitope recognized by the T cells was determined using DNA linkers (depicted as boxed sequence). The single bacteria recognized by the 1H3 T cells all carried a plasmid with a short insert from BRLF1 gene encoding a peptide of 19 aa.

FIG. 4

Identification of Unknown EBV Antigens.

Genomic DNA of EBV was purified, digested with frequently cutting restriction enzymes and small DNA fragments ligated into the bacterial expression vector mix. Liquid bacterial cultures in one 96-well plate were inoculated with 60 cfu/well. Bacterial suspensions were added to APC as described and subsequently probed with the EBV specific T cell clones F7 and G11-3. These T cell clones had been generated by repeated stimulation of PBL with autologous LCL. (A) The T cell clone G11-3 recognized pool B12, which contained one positive colony E1. The plasmid from colony E1 carried a 147 bp insert. The GenBank homology search showed that insert is derived from the BNRF1 gene, encoding a tegument protein of EBV. Using synthetic linkers, the epitope recognized by the T cells was determined (boxed sequence). (B) The T cell clone also recognized a single positive pool A11, of which six positive bacteria colonies were derived. Sequence analysis revealed that all carried the same 66 bp insert derived from the BALF4 gene.

FIG. 5

Efficient Recognition of Bacteria Expressing Antigen-CAT Fusion Proteins but not Whole Proteins.

Bacterial colonies expressing antigen-CAT fusion proteins as well as bacteria expressing the whole ORF of the antigen in the same expression vector were cultured as described and probed with specific T cells. Bacteria expressing antigen-CAT fusion proteins were efficiently recognized over a broad concentration range. By contrast, bacteria expressing the whole ORF of the antigens were recognized not at all or to a much lesser extent, even when the highest concentration of bacteria ($10^8$/well) were used.

FIG. 6

Schematic Depiction of the Expression Vector.

The expression plasmids F288A, B and C are derivatives of the bacterial expression plasmid pTrcHisA (Invitrogen), which contains an IPTG-inducible promoter and translational start site (ATG) for the expression of N-terminally His- and antibody (Anti-Xpress) epitope-tagged fusion proteins. Into this plasmid, the coding sequence of the green fluorescent protein (GFP) was inserted together with a linker coding for a flexible glycine-serine (G-S) peptide and a multiple cloning site (MCS). This MCS contains unique recognition sequences for several restriction enzymes that allow insertion of blunt end antigenic fragments or sticky end DNA linkers. The StuI and the MscI sites are separated by stop codons in all three reading frames (shaded boxes) to prevent GFP expression from non-recombinant plasmids. The plasmids F288A, B and C differ by one or two nucleotides inserted in front of the multiple cloning site only.

FIG. 7

Bacterial Colonies Expressing Antigen-GFP Fusion Proteins are Green.

The coding sequence of EBNA3A was digested with frequently cutting restriction enzymes and ligated into the expression vector mix. After transformation, bacteria were plated on LB agar plates containing antibiotics and 1 mM IPTG. Following overnight incubation, approximately 10% of the outgrowing colonies had a green fluorescent appearance under daylight.

FIG. 8

Identification of the Epitope Recognized by the EBNA3A-Specific T Cell Clone 3A-3D5.

Single green colonies were picked and used to inoculate liquid cultures in five 96 well microtiter plates (I-V). Of each plate, two pools of 48 single colonies (designated A and B) were prepared, and after induction of protein expression, the recombinant His-tagged proteins isolated. (A) PBMC were incubated with the purified protein pools for 24 hours, and then probed with the EBNA3A-specific T cells. The next day, 100 µl of supernatant was assayed for GM-CSF secretion by ELISA. Six of the ten pools tested were positive in the assay. PBMC alone and PBMC incubated with recombinant EBNA3A protein served as controls. (B) Proteins were purified from all 96 single bacterial colonies of master plate 1, from which the positive pools IA and IB were derived, and tested individually. After 24 hours of incubation of LCL with the proteins, the T cell clone 3A-3D5 was added and GM-CSF secretion determined 20 hours later. The bacterial colonies in wells D1 and E5 expressed a protein that stimulated cytokine secretion by the T cells clone. (C). The plasmids from the bacteria D1 and E5 were extracted and the inserts sequenced. The plasmid from colony D1 carried a 45 bp insert derived from HaeIII digest of the EBNA3A CDS, while the insert in colony E5 encompassed 68 bp and was derived from partial digestion of the EBNA3A CDS with a combination of HaeIII and BsaJI. The corresponding amino acid sequence encoded by the inserts is shown underneath. The epitope was verified by testing a synthetic peptide spanning the 16AA overlap in a T cell recognition assay (data not shown).

FIG. 9

Definition of the Epitope Core Sequence Using DNA Linkers.

To define the core sequence of the epitope, five DNA linkers (L1-L6) were synthesized that code for partially overlapping peptides of 12 AA spanning the epitope of EBNA3A (marked in dark grey). The linkers were inserted into the expression vector and the resulting recombinant proteins were purified and tested in a T cell recognition assay (depicted to the right). The linkers L2, 3, 4 and 5 gave rise to proteins that were recognized by the EBNA3A-specific T cell clone 3A-3D5, while the proteins derived from linkers L1 and L6 were not. The EBNA3A peptides encoded by linkers L2-5 overlap in nine amino acids (marked in light grey).

FIG. 10

Antigen Presentation Experiments Using Liquid Cultures of Transformed Bacteria.

Bacteria transformed either with the plasmid D1 encoding the epitope recognized by the EBNA3A-specific T cell clone 3A-3D5, or the plasmid F216 encoding the epitope recognized by the influenza M1-specific T cell clone M1-E5 were grown as liquid cultures and protein expression induced when the cultures reached an $OD_{600}$ of 0.8. The bacteria were harvested four hours later by centrifugation, and resuspended in LB media to an $OD_{600}$ of 5. Different volumes of the bacterial suspensions were added to $1\times10^5$ autologous LCL in 200 µl of LCL media supplemented with 50 µg/ml gentamicin to terminate bacterial growth. After 24 hours of incubation, 100 µl of media was removed and 100 µl LCL media containing $1\times10^5$ CD4+ T cells added and cytokine secretion by the T cells determined 20 hours later by ELISA. The T cells specifically recognized target cells incubated with the relevant but not the control bacterial suspensions over a broad concentration range.

FIG. 11

Identification of a T Cell Epitope within the Membrane Protein gp350.

The coding sequence of gp350 was digested with frequently cutting restriction enzymes and cloned into the expression vector mix as described above. (A) The four protein pools from two 96 well plates were pulsed onto autologous PBMC and the gp350-specific T cell clone gp-B8 was added 24 hours later. A strong activation signal was detected with the protein preparation from pool IA. (B) Bacterial suspension cultures of all 48 colonies of this pool were inoculated and protein expression induced by addition of IPTG. Four hours later, 20 µl from each bacterial culture were transferred directly into separate wells of a 96 well plate seeded with $5\times10^5$ PBMC/well. After 24 hours of incubation, the cells were irradiated (40Gy), and washed. Subsequently, $1\times10^5$ T cells were added per well and IFNγ secretion by the T cells measured by ELISA. A single bacteria colony A8 was identified that expressed a 152 bp fragment of gp350 in frame with the His-tag and with GFP.

FIG. 12

DANI assay plate #2, 60 cfu/well screened with T cell clone C1-9. In this example, the T cell clone did not recognize any of the proteins expressed in the bacterial pools of plate #2. Because T cells secrete cytokines only in response to antigen recognition, no specific signal above background was detected.

FIG. 13

DANI assay plate #3 with 60 cfu/well and C1-9 T cells. The well E3 of plate #3 induced secretion of GM-CSF by the T cells.

FIG. 14

Test of single bacterial colonies of the positive pool 3/E3 with C1-9 T cells. Of 96 single bacterial colonies tested, six were recognized by the T cell clone C1-9.

EXAMPLES

Example 1

In this example, CAT is used as a marker in the fusion protein.

Generation of Expression Vector System

In order to create an expression vector system we inserted the coding sequence of the chloramphenicol acetyltransferase (CAT) gene downstream of the IPTG-inducible promoter in the pTrcHisA plasmid (Invitrogen), fusing a histidine (His)-tag and the AntiXpress antibody epitope to the N-terminus of CAT. The resulting fusion proteins could be purified over nickel columns and expression monitored by Western blotting. For the insertion of antigenic fragments, a multiple cloning site (MSC) was introduced upstream of the CAT open reading frame (ORF). The MSC contains unique recognition sites for four blunt end restriction endonucleases, with the first (StuI) and the last three (MscI, Eco47III and SnaBI), separated by stop codons in all three reading frames to prevent CAT expression from non-recombinant plasmids (FIG. 1A). MscI, Eco47III and SnaBI restriction sites are partially overlapping, cutting the DNA at three different positions of the reading frame. From this vector designated F315A, two additional versions F315B and -C were created, which differ from the parental F315A version by one or two nucleotides inserted in front of the MSC. Thus, by cutting vectors F315A, -B and -C with StuI, any DNA fragments can be inserted in frame with the upstream ORF coding for the His-tag and the antibody epitope. Additional restriction of the vector mix with MscI, Eco47III or SnaBI, allows insertion of any DNA fragment in frame with downstream CAT ORF (FIG. 1A). To test whether N-terminal fusions of CAT would interfere with protein expression and function by interference with proper protein folding, we inserted gene fragments of varying length in frame with CAT, and assayed growth of transformed bacteria on agar plates containing chloramphenicol. Insertion of fragments coding for more than 100 amino acids in front of CAT did not abrogate resistance to chloramphenicol (data not shown). In order to test whether different antigen-CAT fusion proteins were expressed at similar levels, and whether bacterial colonies expressing antigen-CAT fusion proteins in frame could be selected for with chloramphenicol, we randomly ligated blunt-ended short cDNA fragments generated from cDNAs of a human B cell line into the vector mix. Upon transformation, bacteria were plated on agar plates containing chloramphenicol and IPTG and thirteen randomly chosen outgrowing bacterial colonies were used for further analysis. Plasmids were extracted from these colonies and the inserts sequenced. These experiments showed that the size of the inserts ranged from 27-159 bp. Importantly, none of the bacteria contained religated vector without insert, and all except colony #6 expressed fusion proteins consisting of a N-terminal His-tag, the inserted peptide fragment and CAT. In parallel, bacteria lysates of the colonies were separated by SDS-PAGE and the proteins stained with Coomassie® dye, or analyses by Western blot using the AntiXpress antibody (Invitrogen). As already evident from Coomassie staining, all fusion proteins were expressed at similar and very high levels comprising up to 50% of the protein lysate (FIG. 1B). Interestingly, colony #6 expressed a fusion protein that lacked the His-tag and the antibody epitope. Translation of this protein was initiated at an internal ATG within the inserted cDNA fragment. As a consequence, this protein remained undetected in Western blot experiments with the AntiXpress antibody (FIG. 1B).

Efficiency of Antigen Presentation

Figure 2:
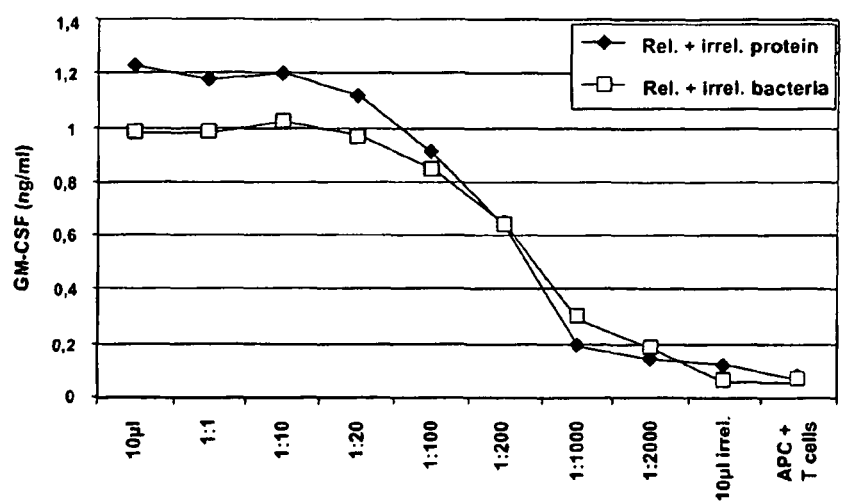

In our previous antigen presentation experiments we noted that human APCs (LCL and PBMC) efficiently present antigens expressed within bacteria on MHC II. Additionally, we showed that T cells specifically recognized target cells incubated with bacterial suspensions over a broad concentration range. To assess sensitivity of this antigen identification approach, we incubated LCL with increasing amounts of bacteria expressing influenza M1 epitope fused to CAT, and, following a 24 hours incubation period, probed the cells with the M1-specific CD4+ T cell clone M1-E5 (Nimmerjahn et al., 2003). To determined efficiency of antigen presentation, we purified the M1-CAT fusion protein from bacterial cultures over nickel columns, and incubated LCL with increasing amounts of proteins in parallel. To simulate screening conditions, we diluted the purified protein and the bacterial suspension in irrelevant protein and bacterial cultures to a final concentration of 500 µg/ml protein and $10^{10}$ bacteria/ml, respectively. Constant amounts of these mixes (10 µl) were added to $1\times10^5$ autologous LCL in 200 µl of LCL media supplemented with 10 µg/ml gentamicin to terminate bacterial growth. After 24 hours of incubation, 100 µl of media was removed and 100 µl T cell media containing $1\times10^5$ CD4+ M1 E5 T cells added and cytokine secretion by the T cells determined 20 hours later. The T cells recognized LCL incubated with whole bacteria or purified protein over a broad concentration range and with similar efficiency even when diluted 1:500 (FIG. 2). These experiments showed that antigens are efficiently detected within large pools and suggested that unknown antigens may be identified with this approach.

Direct Epitope Mapping in Model Antigens

Figure 3:
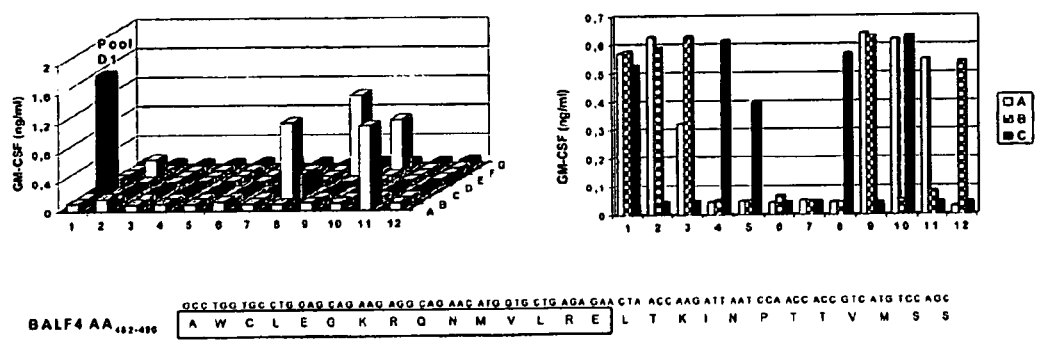
Figure 3:
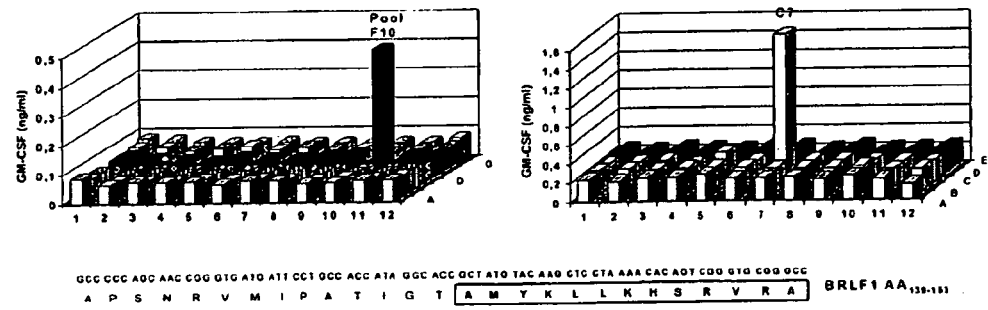
Figure 3C:
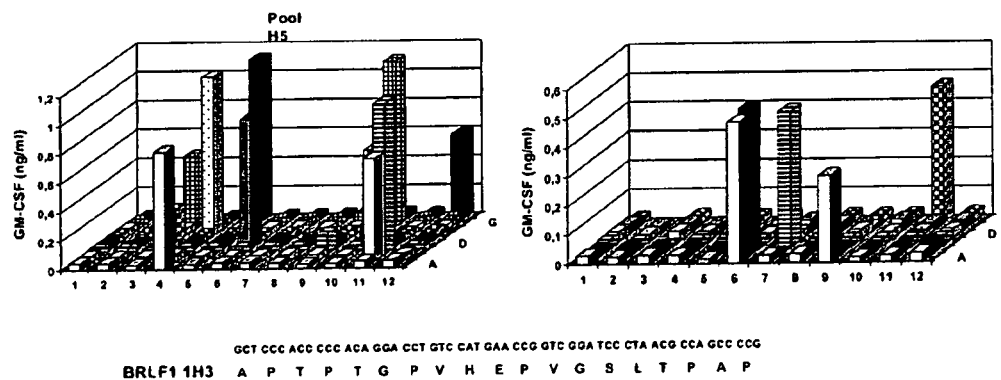

In a first set of experiments we sought to apply this method to define T helper cell epitopes within known antigens. Two CD4+ T cell clones specific for the EBV protein BRLF1 termed 3A10 and 1H3, and one clone specific for the BALF4 protein (clone B5) had been established in our group by stimulating PBMC of latently EBV-infected healthy donors with purified recombinant BRLF1 and BALF4 proteins (Adhikary et al., submitted). The coding sequence of these two antigens were digested with single or combination of frequently cutting restriction enzymes, the resulting short DNA fragments treated with T4 polymerase to generate blunt ends, and ligated into a mix of vectors F315A, -B, and -C digested with StuI and in addition with either MscI, SnaBI, or Eco47III. Following transformation, bacteria were incubated in 96 well microtiter plates in superbroth media containing IPTG and chloramphenicol to select for recombinants that express antigen-CAT fusion proteins. The number of bacterial colony forming units (cfu) per well was determined in parallel by plating aliquots of the transformed bacteria on agar plates containing IPTG and chloramphenicol. These experiments revealed that liquid cultures had been inoculated with were inoculated with 14 cfu/well in the case of BALF4 antigen and 60 cfu/well in the case of BRLF1. Next day, bacteria were transferred into 96 well deep well blocks and harvested by centrifugation when an optical density $OD_{600}$ of 1 was reached. The bacteria were resuspended in ⅕ of the original volume, and from each well 10 µl of were added to $1\times10^5$ LCL in 200 µl of LCL media per well of a microtiter plate. Following overnight incubation, $1\times10^5$ T cells were added and cytokine secretion determined 24 hours later As shown in FIG. 3, five pools were recognized by the BALF4 specific T cell clone B5. In the case of BRLF1, clone 3A10 recognize one whereas clone 1H3 recognized ten pools indicating that the two clones recognize different epitopes. To identify single positive bacteria, the positive pools were plated on agar plates containing 1 mM IPTG and 30 µg/ml chloramphenicol, and after overnight incubation single bacteria colonies were picked, expanded, and tested with the T cells as described. Plasmids from positive bacteria were extracted and the inserts sequenced. All five single positive bacteria of pool D1 analysed carried the same plasmid that coded for a BALF4 peptide of 27 aa. The only bacterial colony recognized by clone 3A10 carried a fragment of 81 bp derived from BRLF1 coding for a peptide of 27 aa. All five single colonies derived from pool H5 and recognized by clone 1H3 expressed an identical peptide of 19 aa from BRLF1 (FIG. 3). To precisely map the T cell epitopes, we used synthetic linkers spanning overlapping parts of the identified peptides essentially as described in the DEPI assay.

Identification of Unknown EBV Antigens within an EBV Expression Library

Figure 4:
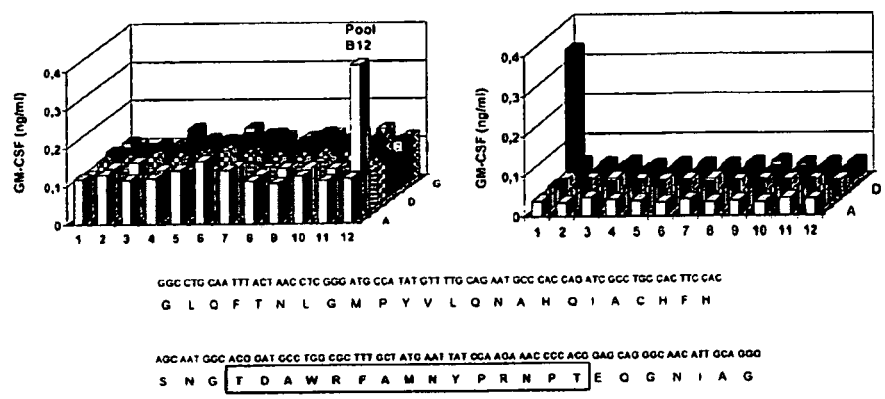
Figure 4:
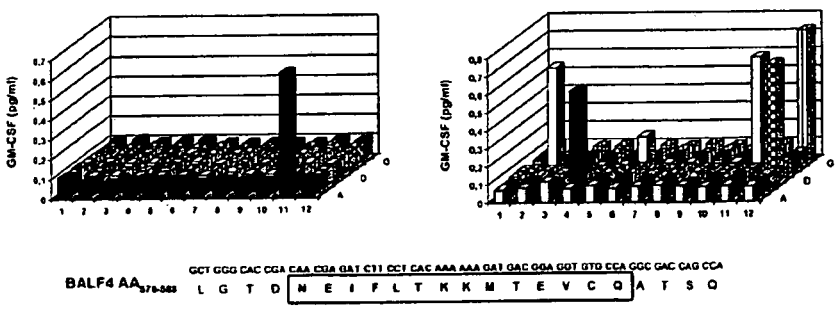

These data suggest that unknown antigens could be identified in more complex libraries. The cell clones specific for EBV had been established in our group by repeated stimulation of CD4+ T cells with autologous LCL, but the specificity of these clones had remained unknown. In a second set of experiments we therefore tested whether this method could be used to identify unknown viral antigens. Genomic DNA of EBV was isolated and digested the DNA with frequently cutting restriction enzymes. The resulting short DNA fragments were randomly ligated into the CAT selection vector system as described. With an average insert size of 82 bp in previous experiments and a genome size of 182 kb, one 96 well plate seeded with 60 cfu/well would cover the whole EBV genome 2.5 times. Therefore, we sought to identify the antigens recognized by the EBV-specific T cell clones G11-3 and F7 by plating the EBV library at 60 cfu/well in one 96 well plate. As shown in FIG. 4, both clones recognized a single but different bacterial pool. All single positive bacterial colonies recognized by T cell clone F7 carried a plasmid with a 66 bp fragment from the BALF4 gene expressed in frame with the His-tag and CAT. Using synthetic linkers, the core epitope sequence was subsequently defined as $AA_{575-589}$ DNEIFLTKKMTEVCQ (SEQ ID NO.: 1). Clone G11-3 only recognized one single bacteria colony carrying a plasmid containing a 147 bp fragment of the BNRF1 gene. The core epitope sequence was defined in subsequent experiments as $AA_{1238-1252}$ TDAWRFAMNYPRNPT (SEQ ID NO.: 2). These results demonstrated that unknown viral antigens can be identified with this method.

Figure 5:
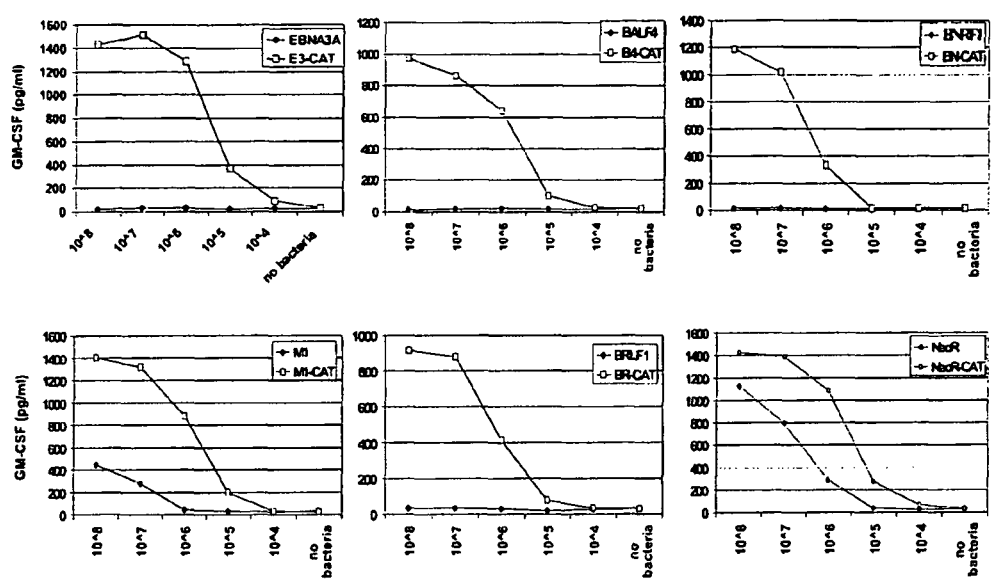

Efficient Recognition of Bacteria Expressing Antigen-CAT Fusion Proteins but not Complete Antigens Bacterial expression of whole cDNAs has been successfully applied to identify a MHC II-restricted murine minor histocompatibility antigen. To compare efficiency and sensitivity of the two approaches, we sought to compare T cell recognition of various antigens expressed as full length proteins or as short antigenic fusion proteins described here. Therefore, the ORF of the EBV proteins BALF4, BRLF1, EBNA3A, the influenza matrix protein M1, and the NeoR were expressed in frame with the upstream His-tag in the pTrcHis vector. Single bacterial colonies transformed with the plasmids were used to inoculate 400 ml superbroth cultures, and protein induction induced when bacterial suspensions reached an $OD_{600}$ of 0.8. Four hours later, the bacteria were harvested by centrifugation and resuspended at an optical density $OD_{600}$ of 5. Various dilutions of this suspension were added to $1\times10^5$ APC and subsequently probed with antigen-specific T cells. In parallel, protein was purified from the rest of the cultures and analysed by Western blot using the AntiXpress antibody. As shown in FIG. 5, all bacteria expressing antigen-CAT fusion proteins were efficiently recognized over a broad concentration range. Of the bacteria transformed with plasmids expressing whole cDNAs, only bacteria transformed with influenza M1 and NeoR expression plasmids were recognized by the T cells, but to a much lesser extent than the fusion constructs. Bacteria transformed with plasmids encoding the EBV proteins BALF4, BRLF1 and EBNA3A were not recognized. These results correlated with a low or undetectable expression of the proteins by Western blot (data not shown), and demonstrated that antigens are efficiently detected with this method even when derived from proteins that are poorly expressed in bacteria.

Because T helper cells play a crucial role in the orchestration of adaptive immune responses, the identification of antigens recognized by CD4+ T cells is important for understanding and enhancing antigen-specific responses. Here, we adapted our previously developed DEPI (direct epitope identification) assay to the identification of unknown antigens. The DANI (direct antigen identification) method is based on the expression of small DNA fragments fused to CAT in bacteria. Bacteria expressing the antigenic fragment in frame with CAT are selected for with chloramphenicol, and added directly to cultures of LCL which efficiently present peptides derived from bacterially expressed proteins on MHC II.

Analysis of single bacteria colonies selected with chloramphenicol demonstrated that all fusion proteins were highly expressed, comprising up to 50% of the total bacteria lysate. By analysing a large number of colonies we never found bacterial colonies carrying religated vector. Furthermore, no inserts shorter that 25 bp were detected although such fragments must have been generated by restriction enzyme digest. Probably these fragments which would code for incomplete class II epitopes were lost during the DNA preparation process involving phenol/chloroform extractions and ethanol precipitations. Fragments bigger than 300 bp were also not detected either because the ligation efficiency drops with size of the insert or larger inserts impair CAT function, e.g. by interfering with protein folding. In almost all colonies the inserts were expressed in frame with the upstream His-tag and the downstream ORF of CAT. In one case, the insert was not expressed in frame with the upstream His-tag, but due to initiation of translation at an internal ATG, the insert was in frame with CAT, confirming the high selection efficiently of the vector system.

Using frequently cutting restriction enzymes we generated small DNA fragments that code for peptides of 10-30 AA, the typical length of peptides presented on MHC class II molecules. The size of DNA fragments generated depends on the restriction endonucleases used. Cleavage of the DNA into small fragments inherently bears the risk of epitope destruction. Thus, different frequently cutting restriction enzymes, alone and in combinations were used to cleave the DNA partially and to completion. Because blunt-ended DNA fragments are ligated into the vector, the antigenic fragment may be expressed in any of the six (sense and antisense) possible reading frames. Thus, 5/6 bacteria should express irrelevant proteins. However, the genetic code uses 64 codons including three stop codons. Thus, except for natural ORF, fragments translated in irrelevant reading frames should terminate statistically after 64 bp. In the sequence analysis described here, we did not find colonies expressing fusion proteins in which the insert was expressed in an irrelevant reading frame. In additional experiments performed meanwhile, we did find such colonies, though at low frequency. The number is strongly dependent on the average insert size. The shorter the DNA inserts, the higher the number of colonies expressing inserts in irrelevant reading frames. On the other hand, increasing the insert size bears the risk of interference with CAT function or reduction in protein levels. To our experience, an average insert size of about 90 bp is best suited to identify antigens with this approach.

As APC for the presentation of peptides derived from bacterially expressed proteins on MHC II LCL were used. LCL express high levels of MHC class II molecules and can be obtained from small blood samples. Using autologous LCL as APC also offers the advantage that knowledge of the restriction molecule is not required. LCL efficiently ingest and present antigen expressed in whole intact bacteria, leading to T cell recognition even when diluted 1:500 in irrelevant bacteria. In the experiments described we have chosen more conservative pool sizes, first because with a pool size of 60 cfu/well the whole EBV genome is covered more than twice in one 96 well plate, and larger pool sizes would require testing of a larger number of single colonies from positive pools. Due to the high sensitivity of the method much larger pool sizes may be used when screening more complex libraries.

Although the identification of MHC class II-restricted antigens by bacterial expression of cDNAs has been described (Sahara and Shastri, 2003), the expression level of eukaryotic proteins in bacteria may vary over several orders of magnitude, making representative pool sizes difficult to establish. While large pool sizes may be successfully used to identify highly expressed antigens, the identification of most antigens will require much smaller pool sizes. In our experiments several antigens remained undetected even when undiluted bacteria were used, implicating that some antigens will remain undiscovered with this method.

In the DANI assay described here, all antigenic fragments are expressed equally well in bacteria, irrespectively of the protein from which they are derived. Thus, representative pool sizes for all antigens may be established. In addition, frozen expression libraries can be repeatedly used. Moreover, the small size of the antigenic peptides greatly facilitates the definition of the T cell epitopes. This high sensitivity and simplicity indicate that this method may not only be used for the identification of bacterial or viral antigens, but may also be applied to identify antigens within complex cDNA libraries.

Materials and Methods

Bacterial Strain and Culture

The *Escherichia coli* strain XL-1 Blue MRF' (Stratagene) was used in all experiments described. Bacteria were cultured in a bacterial incubator or, as liquid cultures, in a bacterial shaker at 37° C. Appropriate concentrations of antibiotics (100 µg/ml ampicillin, 15 µg/ml tetracycline and 30 µg/ml chloramphenicol) were used for selection. For long-term storage of bacteria, glycerol was added to dense bacterial cultures to a final concentration of 20% and stored at −80° C. Protein expression was induced by addition of isopropyl-βD-thiogalactopyranoside (IPTG) at a final concentration of 1 mM.

Construction of Expression Vector

All DNA manipulations were done according to standard procedures (Sambrook et al., 2001). To generate an expression vector that allowed insertion of antigenic fragments between the His-tag at the amino-, and CAT at the carboxy-terminus, the open reading frame of CAT was first cloned into the BamHI-HindIII sites of the bacterial expression vector pTrcHisA (Invitrogen) to yield plasmid CAT-pTrcHisA. Using site directed mutagenesis, the MscI site within the CAT ORF was destroyed without altering the amino acid sequence, yielding plasmid CAT-pTrcHisA^Msc. Into this plasmid, a multiple cloning site was introduced immediately upstream of the ORF of CAT by inserting a DNA linker into the unique BamHI restriction site, giving rise to plasmid F315A (oligo F315 sense: GATCCGAGCTCGAGGCCTAATTAGCTGATGGCCAGCGCTACGTACCG (SEQ ID NO.: 3) oligo F315 anti:GATCCGGTACGTAGCGCTGGCCATCAGCTAATTAGGCCTCGAGCTCG (SEQ ID NO.: 4)). This plasmid was cut with XhoI and partially with BamHI. Two different linkers were inserted into this plasmid, causing a shift in the reading frame by +1 or +2 positions (FIG. 1). These two additional versions of the vector were designated F315B and F315C. The linkers were prepared by mixing equimolar amounts (100 pmol/µl) of sense and antisense oligos. To form double stranded linkers, the mix was heated to 95° C. for 5 min, and then allowed to cool down slowly to room temperature. 1 µl of hybridized linker was then ligated with 300 ng of vector digested with the indicated restriction enzymes. Integrity of all plasmids was verified by restriction enzyme digest and sequence analysis of the modified regions.

For insertion of antigenic DNA fragments into the expression vector, equal amounts of the plasmids F315A, B, and C were mixed and cut with StuI. Following phenol/chloroform extraction the linearized plasmids were divided into three samples which were then digested with either MscI, Eco47111, or SnaBI, and CIP treated to prevent relegation of the vector. After phenol/chloroform treatment, the vector DNA was separated in an agarose gel and purified using Qiaex 11 gel extraction kit (Qiagen).

Generation of Expression Library

The open reading frames encoding BRLF1 and BALF4 were digested with chosen frequent cutters and if necessary treated with T4 polymerase to form blunt ends. The λ-phage DNA was purified using Lambda Maxi Kit according to the guidelines of the manufacturer (Qiagen). The B cell λ-phage library was generated previously in our lab using λZAPII cDNA Gold cloning kit (Stratagene). EBV DNA was obtained according to protocol described at http://haema145.gsf.de/ham/medpre.htm. Briefly, 6×400 ml dense bacterial cultures, transformed with p2089, a F-factor derived plasmid containing the whole EBV genome, were centrifuged for 10 min at room temperature at 5000×g. Lysis of bacteria and DNA preparations were done by the alkaline lysis method (Sambrook et al., 2001). The purified DNA was dissolved in 5 ml special TE buffer (50 mM Tris pH 8.0, 20 mM EDTA) to which 6.0 g of solid cesium chloride (CsCl) were added and dissolved. After addition of 0.5 ml ethidium bromide (EtBr) stock solution (10 mg/ml) the solution was filled into a 11 ml Kendo Ultra-crimp tube. The tube was centrifuged in a Beckman 70.1 TI rotor at 147,000×g at 20° C. for 48 hours. Two clearly visible bands were collected using a 5 ml syringe and a 1 mm diameter needle (20 G). The collected aliquot was transferred into a new 11 ml ultracentrifuge tube filled with 1.55 g/ml CsCl solution and centrifuged again at 147,000×g at 20° C. for 48 hours. The DNA was again collected using 5 ml syringe and EtBr removed using $H_2O$- and CsCl-saturated isopropanol. EBV DNA was precipitated using isopropanol, and dissolved in 1×TE buffer. Following digestion of the DNA with frequently cutting restriction enzymes and T4 polymerase treatment to generate blunt ends, the DNA was phenol/chloroform extracted, and the concentration determined by spotting serial dilutions of the DNA on an EtBr agarose plate together with DNA of known concentrations and comparing fluorescence intensity under UV light. The frequently cutting restriction enzymes used in this study were: AciI, CviJI*, and MnlI (all from Biolabs except CviJI* from EurX). 100 ng of this digested DNA were ligated overnight at 16° C. into 300 ng of expression vector in a total volume of 10 µl. To determine ligation and transformation efficiency, 1 µl of the ligation reaction was used to transform XLI-Blue MRF' and the number of outgrowing colonies on LB agar plates containing 1 mM IPTG and 30 µg/ml chloramphenicol counted. For library generation, indicated numbers of cfu were used to inoculate liquid cultures of superbroth media containing 1 mM IPTG and 30 µg/ml chloramphenicol in 96 well plates. After overnight cultivation, 100 µl of bacterial suspension from each well was transferred into 1.5 ml superbroth medium/well containing 1 mM IPTG and 30 µg/ml chloramphenicol in 96 deep well plate (Peqlab). To the rest of the bacterial culture in microtiter plates, 100 µl of superbroth media containing 40% glycerol was added, and the plates frozen as mother plates at −80° C. The bacterial pools in deep well plates were incubated under vigorous agitation at 37° C. in a bacterial shaker. When the optical density of the wells reached an $OD_{600}$ of 1, the bacteria were harvested by centrifugation (3000 rpm for 15 min) and the pellet resuspended in 300 µl of medium. 10 µl of these bacterial suspensions were added to $1×10^5$ APC in 200 µl medium/well of a 96 well microtiter plate. After 24 hours of incubation, 100 µl of medium was discarded and $1×10^5$ specific CD4+ T cells added/well in 100 µl T cell medium containing 100 µg/ml gentamicin. GM-CSF secretion upon specific recognition was measured 24 hours later by ELISA assay using 100 µl supernatant.

The minimum number of colonies to screen was calculated depending on the number of restriction sites within the open reading frame of the antigen. For example, the ORF of BRLF1 is 1818 bp. Complete digestion of the coding sequence with the restriction enzyme CviJI* generates 57 fragments. Because the DNA fragments may be inserted in either orientation, a given fragment may be expressed as His-tagged CAT fusion proteins in six different reading frames. Thus, the minimum number of colonies to pick is 57×6. Because insertion of a fragment in an irrelevant reading frame may cause termination of translation, the actual number turned out to be much lower. In addition, the DNA was digested to completion or partially with combinations of enzymes.

Protein Expression and Purification

To isolate bacterially expressed proteins, bacteria were incubated in superbroth medium containing 1 mM IPTG and 30 µg/ml chloramphenicol under vigorous agitation at 37° C. in a bacterial shaker. When the cultures reached an optical density $OD_{600}$ of 0.8, the bacteria were centrifuged (3000×g/15 min) and the pellet resuspended in 50 ml of lysis buffer (100 mM $NaH_2PO_4$, 10 mM Tris-HCl, 8M urea, 10 mM imidazole, 0.05% Tween 20, pH 8.0). Following centrifugation (5000×g/15 min) to pellet insoluble bacterial debris, the supernatant was transferred to a new tube and 300 µl of Nickel-NTA agarose (Qiagen) added. His-tagged proteins were allowed to bind to the nickel-coated agarose by overnight incubation at 4° C. under constant agitation. Next day, the Nickel-NTA agarose beads were pelleted by centrifugation (2000×g/10 min), and washed once with lysis buffer. To elute the proteins, the beads were incubated three times with 30041 of elution buffer (lysis buffer with 500 mM imidazole, pH 7.5) and the protein-containing supernatant collected after each incubation step by centrifugation (10,000×g/3 min). The pooled eluate was dialysed against PBS for two days. 10 µl of this protein solution, typically containing 500 µg/ml protein, were added to APC in 200 µl in a well of a microtiter plate.

The proteins were separated by SDS-PAGE and identity and purity analysed by Coomassie staining and by Western blot using the AntiXpress antibody (Invitrogen) and the ECL plus detection system (Amersham Biosciences).

T Cell Clone Isolation and Cultivation

Generation of specific T cell lines and isolation and expansion of CD4+ T cell clones have been described previously (Mautner et al., 2004). The following T helper cell clones were used in this study: M1-E5 recognizing influenza M1 $AA_{234-248}$-LENLQAYQKRMGVQL (SEQ ID NO.: 5). The epitopes of recognized by the BRLF1-specific T cell clones 3A10 and 1H3 were identified in the present work. The clones G11-3 and F7 were isolated from EBV-specific T cell lines generated by repeated stimulation of peripheral blood CD4+ T cells with autologous LCL. Cytokine secretion assays were performed as described (Mautner et al., 2004). Briefly, $1\times10^5$ LCL or $5\times10^5$ PBMC were seeded per well of a 96 well flat bottom plate in 200 µl of LCL media (RPM' 1640 supplemented with 2 mM L-glutamine, 1% non-essential amino acids, 1 mM sodium pyruvate, 100 µg/ml gentamicin, 10% FCS). The cells were incubated for 24 hours either with purified proteins or whole bacteria. At the end of the incubation period, 100 µl of supernatant was removed and $1\times10^5$ T cells in 100 µl LCL media added. Cytokine secretion by the T cells was measured 20 hours later by ELISA (R&D Systems).

Analysis of Positive Bacterial Colonies

Single positive bacterial colonies were grown overnight and plasmid DNA was isolated according to the guidelines of the manufacturer (Qiagen). Plasmid DNA was sequenced using pTrcHis forward primer (GAGGTATATATTAATG-TATCG; SEQ ID NO.: 6).

Example 2

This example is directed to the expression of a fusion protein, in which GFP is used as a marker.

Design of the Expression Vector

In previous studies we had mapped epitopes within antigens recognized by Epstein-Barr virus-specific CD4+ T cells by expressing deletion constructs of the antigens in bacteria. Following protein purification, the antigen fragments were fed to antigen presenting cells, which were then probed with antigen-specific T cells. Those proteins still containing the epitope were identified by measuring cytokine secretion of the T cells and were subsequently further trimmed and tested in the same way (Mautner et al., 2004). This procedure eventually faced the problem that small proteins are unstable and thus difficult to express in bacteria. Therefore, we fused small antigen fragments to the green fluorescent protein (GFP), which is efficiently expressed in bacteria. Moreover, bacterial colonies expressing antigen-GFP fusion proteins appear green, which greatly facilitates the identification of bacterial recombinants. These experiments suggested that epitopes may be identified directly by screening antigen-GFP expression libraries created by randomly fusing antigen fragments to GFP, and the green appearance of antigen-GFP proteins expressing bacterial colonies would aid at reducing the screening effort.

Figure 6:
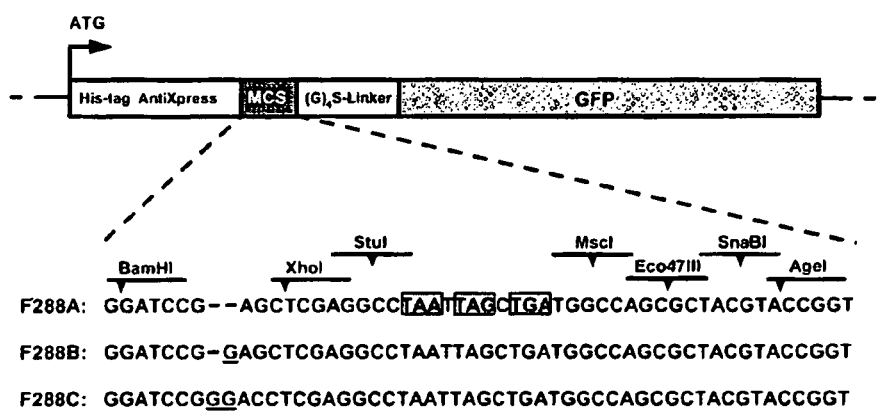

In order to create a plasmid that would allow for the expression of such chimeric proteins, the coding sequence of GFP was inserted downstream of the IPTG-inducible promoter in the pTrcHisA plasmid (Invitrogen), fusing a histidine (His)-tag and the AntiXpress antibody epitope to the N-terminus of GFP. Thus, the resulting fusion proteins could be purified over nickel columns and expression monitored by Western blot. Between the antibody epitope and GFP, a DNA linker was inserted that codes for a flexible glycine-serine $(G)_4$-S-$(G)_4$-S-$(G)_4$ peptide linker (Kortt et al., 2001) intended to prevent upstream protein sequences to interfere with GFP folding, as well as a multiple cloning site (MCS) for the insertion of antigen fragments (FIG. 6). This MCS introduces unique recognition sequences for four blunt end restriction endonucleases, with the first (StuI) and the last three recognition sites (MscI, Eco47III, SnaBI), separated by stop codons in all three reading frames to prevent GFP expression from non-recombinant plasmids. The latter three restriction sites are partially overlapping, cutting the DNA at three different positions of the reading frame. Of this cloning vector designated F288A, two additional versions were created. The plasmids F288B and F288C differ from F288A only by one or two nucleotides inserted in front of the multiple cloning site, respectively. Thus, by either cutting vector F288A, B or C with StuI, any DNA fragment can be inserted in frame with the upstream open reading frame of the His-tag and the antibody epitope. By digesting the vector in addition with MscI, Eco47III or SnaBI, the gene fragment may also be inserted in frame with the downstream ORF of GFP (FIG. 6).

To test this new expression vector system, we sought to determine the epitope recognized by an EBNA3A-specific CD4+ T cell clone that had been established by stimulating PBMC of a latently EBV-infected healthy donor with purified EBNA3A protein (Mautner et al., submitted). The coding sequence of the EBNA3A gene was digested with single, or combinations of frequently cutting restriction enzymes, the resulting DNA fragments treated with T4 polymerase to generate blunt ends, and ligated into the vector. To allow insertion of the gene fragments in all possible reading frames, the vector was prepared by digesting an equimolar mix of the plasmids F288A, B, and C with StuI, and in addition with either MscI, Eco47III or SnaBI, followed by calf intestinal phosphatase (CIP) treatment to prevent relegation of the vector.

Expression Library Screening Procedure

Figure 7:
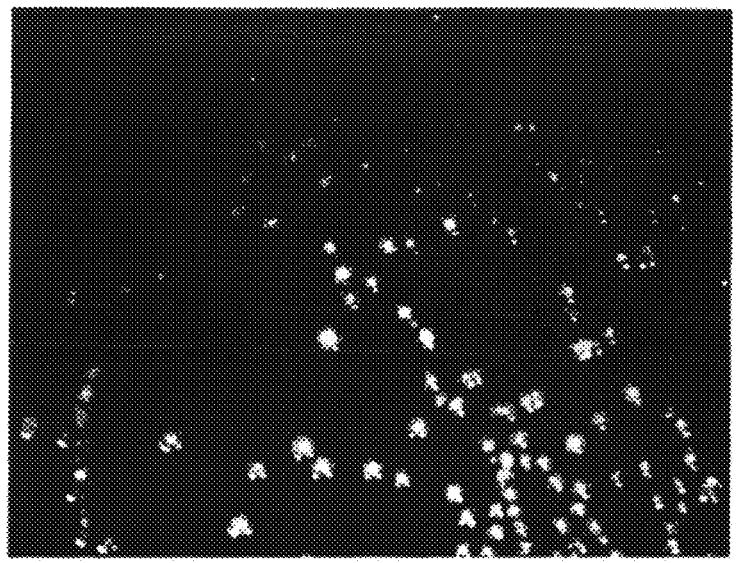

After transformation with the ligated DNA, bacteria were plated on agar plates containing 1 mM IPTG to induce protein expression. Approximately 10% of the resulting bacterial colonies were green (FIG. 7). This was expected because statistically one in nine fragments will be expressed in frame with the upstream ORF coding for the His-tag as well as the downstream ORF coding for GFP. To test this prediction, 20 green and 20 white colonies were picked and the DNA inserts sequenced. In plasmids extracted from green colonies, the DNA inserts were all in frame with GFP, and except for one case also in frame with the upstream ORF coding for the His-tag and the antibody epitope. In the exceptional case, translation had initiated at an ATG codon within the DNA insert that was in frame with GFP and gave rise to an antigen-GFP fusion protein that lacked the His-tag at the N-terminus. By contrast, none of the plasmids isolated from white bacterial colonies coded for His-tagged antigen-GFP fusion proteins. The inserted DNA fragments had shifted the reading frame in all cases, causing premature stop of translation either within the antigen fragment or within GFP. The sizes of the inserts were similar in both groups and ranged between 24-281 bp, depending on the restriction enzyme(s) used to digest the ORF of the antigen. Although DNA fragments shorter than 24 bp should have been created by restriction enzyme digest, no such short DNA inserts were found, most likely because such DNA fragments were lost during preparation of the inserts which involved phenol/chloroform extraction and ethanol precipitation of the digested DNA. This fortuitous loss of short DNA fragments prevented the formation of green bacterial colonies expressing antigen fragments too short for MHC II binding or T cell recognition.

Figure 8:
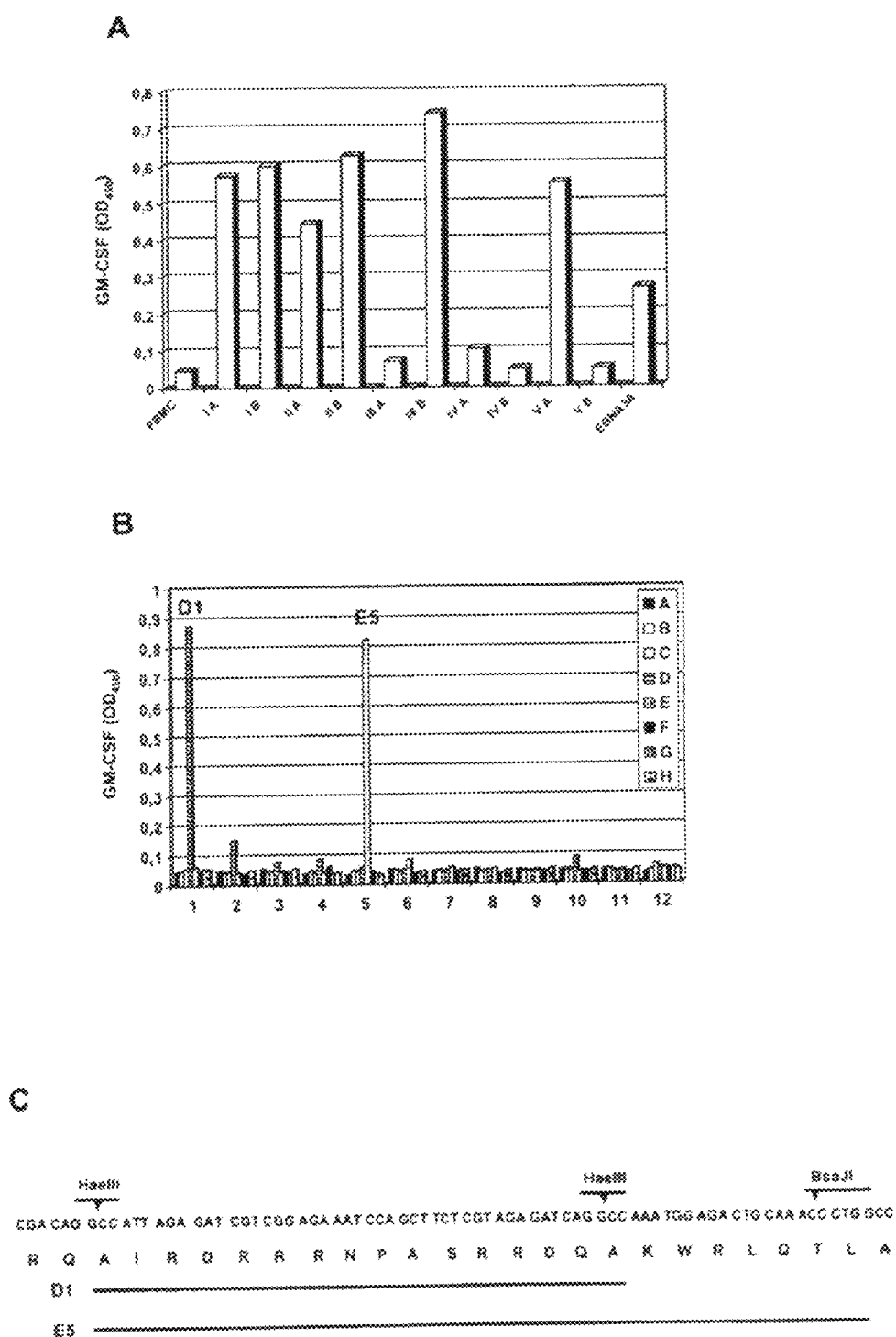

Coomassie® staining of bacterial extracts from green colonies size-separated by SDS-PAGE showed that the expression levels of all green fusion proteins was very high, comprising 10-40% of the protein lysate (data not shown). These results indicated that selection of green colonies might reduce the screening effort ten-fold, and that the uniform and high level of protein expression might facilitate screening of pools of bacterial colonies. To define the epitope recognized by the EBNA3A-specific T cell clone, single green bacterial colonies were picked and transferred into separate wells of a 96 well plate in LB-media. After overnight incubation, aliquots from 48 wells were combined, and protein expression induced by addition of IPTG when the bacterial suspension reached an optical density $OD_{600}$ of 0.8, while the remaining bacterial suspensions in the 96 well plates were frozen as so called "mother plates". A total of five 96 well plates were inoculated with bacteria transformed with expression vector carrying EBNA3A DNA fragments. Proteins from ten pools were purified over Nickel beads and fed to either PBMC or a lymphoblastoid B cell line (LCL) established from the donor, of whom the EBNA3A-specific CD4+ T cell clone was derived. 24 hours later the EBNA3A-specific T cell clone was added and cytokine secretion by the T cells determined 20 hours later by ELISA. As shown in FIG. 8A, six protein pools each derived from 48 green colonies were recognized whereas four pools were not. To identify single positive bacteria, we screened all 96 single colonies from master plate I from which two positive pools were derived. Two proteins purified from wells D1 and E5 were recognized by the T cells (FIG. 8B). Sequencing of the DNA inserts revealed that the plasmid from colony D1 contained a fragment coding for 16 amino acids (AA) of EBNA3A, whereas the plasmid from colony E5 carried a DNA insert encoding 23 AA of EBNA3A. Both fragments overlapped in 16AA and both expressed the fragments in frame with the His-tag and with GFP (FIG. 8C). The T cell epitope was verified with a synthetic peptide covering the overlap. These results demonstrated that this random expression approach can be used for direct epitope mapping.

Definition of Epitope Core Sequences Using DNA Linkers

Figure 9:
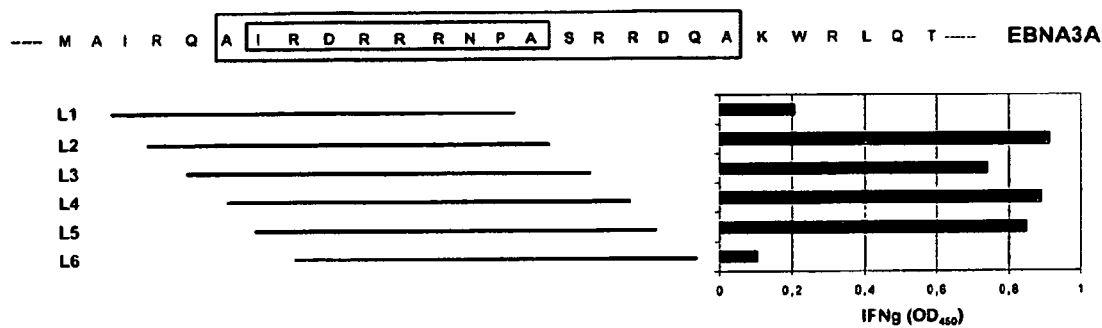
Figure 10:
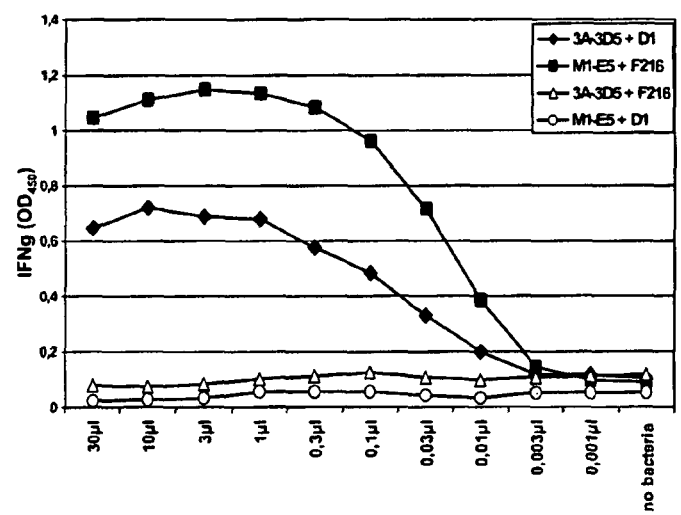

The successful identification of T helper cell epitopes through expression of antigen-GFP fusion proteins suggested that this method could also be applied to map the core sequences of epitopes more precisely and to define amino acids critical for T cell recognition or MHC binding. To test this idea, we synthesized DNA linkers encoding various parts of the EBNA3A epitope. To facilitate ligation of the linkers into the expression vector, two complementary oligonucleotides were synthesized that, upon annealing, generated cohesive ends for ligation into the expression vector digested with the single cutters XhoI and AgeI. Unique recognition sites of these two enzymes flank the MCS (FIG. 6). Following bacterial transformation, several green colonies were picked and the plasmid inserts sequenced. All plasmids carried the synthetic linkers in frame with the His-tag and GFP. The different proteins were expressed and tested in T cell assays (FIG. 9). Using this approach, the core sequence of the epitope recognized by the T cell clone was defined to encompass nine amino acids. Further truncations of this core sequence abrogated T cell recognition, most likely because anchor residues crucial for MHC binding were affected. Thus, amino acids essential for MHC binding and/or T cell recognition can be defined with this method.

Epitope Mapping Using Whole Bacteria

To further simplify the method, we tested whether we could obviate the protein purification procedure to identify single positive bacterial colonies by feeding IPTG-induced bacteria directly to antigen presenting cells. Sahara and Shastri (2003) had shown that mouse dendritic cells could efficiently ingest whole bacteria and present the bacterially expressed antigens on MHC class II. To test whether the human APCs used in this study (LCL and PBMC) could present antigens from whole bacteria with similar efficiency, we performed antigen presentation experiments using liquid cultures of bacteria transformed with plasmids encoding defined T helper cell epitopes. In addition to the EBNA3A-specific T cells, the influenza M1-specific T cell clone M1-E5 and bacteria transformed with the plasmid F216 expressing the M1-epitope fused to GFP was included in this analysis (Nimmerjahn et al. 2003). Protein expression was induced by addition of IPTG when the bacterial suspensions reached an optical density $OD_{600}$ of 0.8. The bacterial cultures were harvested four hours later by centrifugation, and the bacterial pellet was resuspended in LB media to an $OD_{600}$ of 5. 10 μl of such a bacterial suspension contain $10^8$ bacteria. In titration experiments, different amounts of the bacterial suspensions were added to $1\times10^5$ autologous LCL or $5\times10^5$ PBMC in 200 μl of LCL media supplemented with 50 μg/ml gentamicin to terminate bacterial growth. After 24 hours of incubation, 100 μl of media was removed and 100 μl LCL media containing $1\times15$ CD4+ T cells added and cytokine secretion by the T cells determined 20 hours later. Both types of APC efficiently presented the antigen from whole bacteria (FIG. 9). In contrast to LCL, PBMC secreted varying amounts of cytokines when co-cultured with bacteria. Therefore, PBMC were irradiated (40Gy) and washed before addition of the T cells. Importantly, the T cells specifically recognized target cells incubated with bacterial suspensions over a broad concentration range. Thus, fluctuations in the growth rate of single bacterial suspensions within 96 well plates should not impair the sensitivity of the assay. To test this assumption experimentally, a replica of master plate I was prepared by inoculating LB media with the frozen bacterial stocks followed by incubation of the plate at 37° C. in a bacterial shaker. Protein production was induced by addition of IPTG when the first randomly tested wells reached an $OD_{600}$ of approximately 0.8. Four hours later, 20 μl from each well were added directly to $1\times10^5$ LCL in 200 μl of LCL media. The next day, 100 μl of supernatant was removed, and $1\times10^5$ EBNA3A-specific T cells in 100 μl of LCL media were added. Following overnight incubation, IFNγ secretion by the T cells was determined by ELISA. Although the amounts of IFNγ secreted by the T cells were lower when using whole bacteria instead of purified proteins, the results of both experiments were superimposable, demonstrating that whole bacteria can be used to identify single colonies expressing the epitope (data not shown).

Mapping of Epitopes within Proteins Difficult to Express in Bacteria

Figure 11:
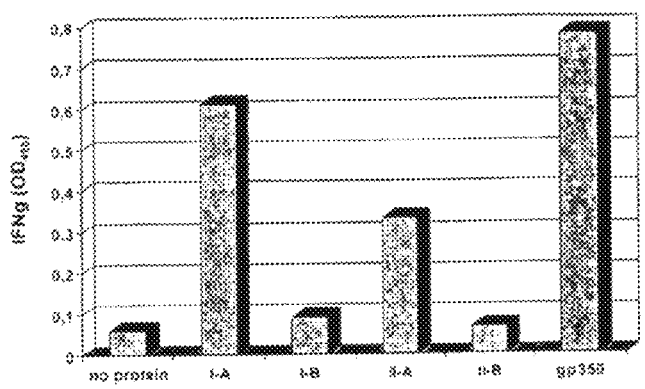
Figure 11:
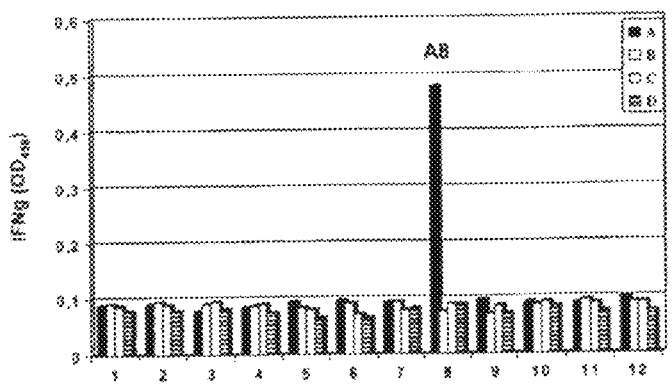

A potential impediment of this epitope identification procedure was the low expression of certain proteins in bacteria. For example, membrane proteins tend to form aggregates, which may result in low or undetectable protein expression. To test whether this method could also be applied to such antigens, we attempted to map the epitope recognized by a gp350-specific CD4+ T cells clone. Gp350 is a glycoprotein of EBV and a major constituent of the viral envelope. During lytic replication of EBV, gp350 is translated into the ER, processed through the Golgi, and targeted to the plasma membrane for envelopment of newly assembled virus particles (Kieff and Rickinson, 2001). As expected, gp350 protein expression in bacteria was undetectable even when His-tagged protein was purified from large scale bacterial cultures over Nickel-NTA columns (data not shown). To test whether the epitope recognized by the gp350-specific CD4+ T cell clone B8 could be identified with the DEPI (direct epitope identification) approach, the coding sequence of gp350 was digested with frequently cutting restriction enzymes and cloned into the expression vector mix as described above. A strong activation signal was detected with the protein preparation from pool IA (FIG. 11A). Bacterial suspension cultures of all 48 colonies of this pool were inoculated and protein expression induced by addition of IPTG. Four hours later, 20 µl from each bacterial culture were transferred directly into separate wells of a 96 well plate seeded with 5×10$^5$ PBMC/well in 200 µl of LCL media, and T cells added the next day. By measuring cytokine secretion of the T cells, a single colony was identified carrying a 152 bp fragment of gp350 (FIG. 11B). Using synthetic linkers spanning this sequence, the epitope recognized by the CD4+ T cell clone B8 was defined as AA$_{65-79}$ FGQLTPHTKAVYQPR (SEQ ID NO.: 7). These results demonstrated that MHC II epitopes may be identified with the DEPI assay even within antigens difficult to express in bacteria.

The DEPI assay described here offers a simple and fast procedure to map epitopes within known antigens. The method is based on the random expression of antigen fragments fused to GFP in bacteria. Owing to their green appearance, recombinant bacteria expressing the antigen-GFP fusion proteins are easily identified, reducing the number of colonies to screen significantly. Furthermore, the high level of protein expression allows to screen large pools of recombinant bacteria, from which single colonies expressing the epitope are identified by feeding whole bacteria directly to APC.

In the DEPI assay, frequently cutting restriction enzymes are used to cleave the open reading frame encoding the antigen into small DNA fragments. Ideally, these DNA fragments should code for peptides of 10-20 amino acids, the typical length of MHC class II-bound peptides. Larger DNA fragments might narrow down but not define the epitope, while shorter fragments might code for partial epitopes only. Because restriction sites are rarely evenly distributed over the coding sequence of the antigen, several different restriction enzymes, either alone or in combinations, are utilised to generate uniformly short fragments. As shown for EBNA3A, cutting DNA with different restriction enzymes also offers the advantage that partially overlapping DNA fragments are created that may help to define the epitope more precisely. Moreover, the potential risk of epitope destruction is greatly reduced when several enzymes with different recognition sequences are used.

The restriction enzyme digest generates blunt ended DNA fragments of varying lengths and in different reading frames. To ensure expression of all fragments, a vector system was designed that accommodates DNA inserts in all possible reading frames. As a consequence, the DNA fragments may be expressed as His-tagged GFP fusion proteins, but only in ⅙ cases in the reading frame of the antigen. Thus, ⅚ green colonies should express irrelevant proteins, increasing the number of colonies to screen fivefold. However, the combination of four nucleotides results in 64 different codons, of which three are stop codons. Thus, except for open reading frames, translation of a randomly chosen DNA sequence will terminate statistically after 64 bp. In the case of EBNA3A, the average insert size of the antigenic fragments was 83 bp. Thus, translation of most of the DNA fragments in irrelevant reading frames should terminate within the DNA fragment and not give rise to green fusion proteins. In fact, within the 20 inserts of green colonies sequenced, all antigen fragments were expressed in the same reading frame as EBNA3A. Thus, the number of colonies to screen should not be increased due to the expression of short alternative reading frames, but should solely depend on the length of the ORF and the average fragment size. In the case of EBNA3A with an ORF of almost 3 kb and an average insert size of 83 bp, roughly every thirty-fifth green colony should express the epitope, provided that the restriction enzymes would leave the coding sequence of the epitope intact. We found expression of the epitope in ⁶⁄₁₀ pools, with each pool consisting of 48 green colonies. Assuming that each positive pool contained only one positive clone, this would result in ⅙₀ green colonies expressing the epitope. This number is higher than calculated, either because some pools contained more than one positive clone, the epitope was destroyed by CviJI* restriction enzyme digest, or some short fragments were translated in alternative open reading frames. However, the number was much lower than expected if the inserted fragments were expressed in all possible reading frames. Similar results were obtained when seven additional epitopes were identified with the DEPI assay (Mautner et al., submitted), further demonstrating the high efficiency of this approach. Moreover, MHC class I-restricted T cell epitopes have been identified within proteins expressed from alternative open reading frames of known genes (Aarnoudse et al., 1999). If such alternative gene products also give rise to MHC class II-restricted epitopes, they may be identified by this random expression approach as well.

It has been reported previously that mouse dendritic cells are capable of ingesting whole bacteria and presenting peptides derived from bacterial proteins on MHC class II (Sahara and Shastri, 2003). These results prompted us to test if the protein purification step could be omitted by incubating LCL or PBMC directly with live recombinant bacteria. Both types of APC were capable of presenting bacterially expressed antigens efficiently on MHC class II. Moreover, recognition occurred over a broad concentration range, so that fluctuations in the growth rate of single colonies in 96 well plates are unlikely to diminish the sensitivity of the assay. However, probably in response to innate immune recognition of microbial components, PBMC often secreted substantial amounts of cytokines upon incubation with bacteria, including IFNγ and GM-CSF. This background of cytokines is easily abrogated by irradiating (40Gy) and washing the cells after incubation with bacteria. The two types of APC, PBMC and LCL, were chosen because both have been shown to present exogenous antigens efficiently on MHC class II (Mautner et al., 2004) and, in contrast to dendritic cells, both can be obtained from small blood samples. Thus, even in cases where clinical material is limited, the DEPI assay may be performed with APC from the same donor from whom the T cells have been established. This allows epitope mapping without knowledge of the T cell restriction element.

Thus, the DEPI assay offers a simple and fast method for the identification of MHC II epitopes, even within proteins difficult to express in bacteria. Insertion of synthetic linkers instead of gene fragments into the expression vector allows to map epitopes precisely and to assess the role of single amino acids in T cell recognition or MHC binding. Moreover, the high sensitivity and simplicity of the DEPI assay warrant further experiments to adapt this method to additional applications, e.g. the definition of epitopes recognized by antibodies, or the identification of unknown antigens.

Materials and Methods

Bacterial Strain and Culture

See Example 1

Construction of Expression Vector

All DNA manipulations were done according to standard procedures (Sambrook et al., 2001). To generate an expression vector that allowed insertion of antigenic fragments between the His-tag at the amino-, and GFP at the carboxy-terminus, the open reading frame of GFP was first cloned into the KpnI-HindIII sites of the bacterial expression vector pTrcHisA (Invitrogen) to yield plasmid GFP-pTrcHisA. Into this plasmid, a multiple cloning site was introduced immediately upstream of the ORF of GFP by inserting a DNA linker into the unique AgeI and XhoI restriction sites, giving rise to plasmid F250A (oligo F250 sense: TCGAGGCCTAATT-AGCTGATGGCCAGCGCTACGTA (SEQ ID NO.: 8); oligo F250 anti:CCGGTACGTAGCGCTGGCCAT-CAGCTAATTAGGCC (SEQ ID NO.: 9)). This plasmid was digested with AgeI and partially with NcoI and a DNA linker coding for a glycine-serine $(G)_4S(G)_4S(G)_4$ peptide linker inserted (oligo F288 sense: CCGGTGGCGGCGG-GAGCGGGGGCGGGGGCAGCGGGGGCGGGGG (SEQ ID NO.: 10); oligo F288 anti:CATGCCCCCGCCCCCGCT-GCCCCCGCCCCCGCTCCCGCCGCCA (SEQ ID NO.: 11)). This plasmid designated F288A was cut with XhoI and partially with BamHI. Two different linkers were inserted into this plasmid, causing a shift in the reading frame by +1 or +2 positions (FIG. 1). These two additional versions of the vector were designated F288B and F288C.

The linkers were prepared by mixing equimolar amounts (100 pmol/μl) of sense and antisense oligos. To form double stranded linkers, the mix was heated to 95° C. for 5 min, and then allowed to cool down slowly to room temperature. 1 μl of hybridized linker was then ligated with 300 ng of vector digested with the indicated restriction enzymes. Integrity of all plasmids was verified by restriction enzyme digest and sequence analysis of the modified regions.

For insertion of antigenic DNA fragments into the expression vector, equal amounts of the plasmids F288A, B, and C were mixed and cut with StuI. Following phenol/chloroform extraction the linearized plasmids were divided into three samples which were then digested with either MscI, Eco47III, or SnaBI, and CIP treated to prevent relegation of the vector. After phenol/chloroform treatment, the vector DNA was separated in an agarose gel and purified using Qiaex II gel extraction kit (Qiagen).

Generation of Expression Library

The open reading frames encoding EBNA3A and gp350 were digested with chosen frequent cutters and if necessary treated with T4 polymerase to form blunt ends. The frequently cutting restriction enzymes used in this study were: AciI, BsaJI, CviJI*, HaeIII, and MnlI (all from Biolabs except CviJI* from EurX). 100 ng of this digested DNA were ligated overnight at 16° C. into 300 ng of expression vector in a total volume of 10 μl. Next day, 1 μl of the ligation mix was used to transform XL1-Blue MRF, and the transformed bacteria plated on LB agar plates containing antibiotics and 1 mM IPTG. Green colonies were picked with sterile tips and transferred to single wells of 96 well plates filled with 200 μl Superbroth media supplemented with antibiotics and incubated overnight at 37° C. The minimum number of green colonies to screen was calculated depending on the number of restriction sites within the open reading frame of the antigen. For example, the ORF of EBNA3A is 2835 bp. Complete digestion of the coding sequence with the restriction enzyme HaeIII generates 35 fragments. Because the DNA fragments may be inserted in either orientation, a given fragment may be expressed as His-tagged GFP fusion proteins in six different reading frames. Thus, the minimum number of colonies to pick is 35×6. Because insertion of a fragment in an irrelevant reading frame may cause termination of translation, the actual number turned out to be much lower (see Discussion). From each 96 well plate, two pools of 48 colonies were made by transferring 100 μl of bacterial culture from each well to 400 ml of Superbroth media. To the rest of the bacterial culture in microtiter plates, 100 μl of LB media containing 40% glycerol was added, and the plates frozen as mother plates at 80° C. The bacterial pools were incubated under vigorous agitation at 37° C. in a bacterial shaker and protein expression was induced by addition of IPTG when the cultures reached an optical density $OD_{600}$ of 0.8. Four hours later, the bacteria were centrifuged (3000×g/15 min) and the pellet resuspended in 50 ml of lysis buffer (100 mM $NaH_2PO_4$, 10 mM Tris-HCl, 8M urea, 10 mM imidazole, 0.05% Tween 20, pH 8.0). Following centrifugation (5000×g/15 min) to pellet insoluble bacterial debris, the supernatant was transferred to a new tube and 300 μl of Nickel-NTA agarose (Qiagen) added. His-tagged proteins were allowed to bind to the nickel-coated agarose by overnight incubation at 4° C. under constant agitation. Next day, the Nickel-NTA agarose beads were pelleted by centrifugation (2000×g/10 min), and washed once with lysis buffer. To elute the proteins, the beads were incubated three times with 300 μl of elution buffer (lysis buffer with 500 mM imidazole, pH 7.5) and the protein-containing supernatant collected after each incubation step by centrifugation (10,000×g/3 min). The pooled eluate was dialysed against PBS for two days. 10 μl of this protein solution, typically containing 500 μg/ml protein, were added to APC in 200 μl in a well of a microtiter plate.

When whole bacteria were fed to APC, bacterial cultures in 96 well plates were used to inoculate deep well plates (Peqlab) containing 1.5 ml/well Superbroth media and antibiotics. Protein expression was induced by addition of IPTG when the optical density in randomly chosen wells reached an $OD_{600}$ of 0.8. Four hours later, from each well 20 μl of bacterial culture were transferred into single wells of flat bottom microtiter plates seeded with $1\times10^5$ LCL or $5\times10^5$ PBMC/well in 200 μl of LCL media. The APC were incubated with the bacteria for 24 hours. When PBMC were used, the cells were irradiated (40Gy) and washed prior to T cells addition. Subsequently, 100 μl of supernatant per well were removed and $1\times10^5$ T cells in 100 μl LCL media added.

T Cell Clone Isolation and Cultivation

Generation of specific T cell lines and isolation and expansion of CD4$^+$ T cell clones have been described previously (Mautner et al., 2004). The following T helper cell clones were used in this study: 3A-3D5 recognizing EBNA3A $AA_{142-156}$-RQAIRDRRRNPASRR (SEQ ID NO.: 12); gp-B8 recognizing gp350 $AA_{65-79}$-FGQLTPHTKAVYQPR (SEQ ID NO.: 13) and M1-E5 recognizing influenza M1 $AA_{234-248}$-LENLQAYQKRMGVQL (SEQ ID NO.: 14). All T cell clones are HLA-DRB1*1301 restricted. The first two epitopes were identified in this work. Cytokine secretion assays were performed as described (Mautner et al., 2004). Briefly, $1\times10^5$ LCL or $5\times10^5$ PBMC were seeded per well of a 96 well flat bottom plate in 200 μl of LCL media (RPMI 1640 supplemented with 2 mM L-glutamine, 1% non-essential amino acids, 1 mM sodium pyruvate, 50 μg/ml gentamicin and 10% FCS). The cells were incubated for 24 hours either with purified proteins or whole bacteria. At the end of the incubation period, 100 μl of supernatant was removed and $1\times10^5$ T cells in 100 μl LCL media added. Cytokine secretion by the T cells was measured 20 hours later by ELISA (R&D Systems).

Analysis of Positive Bacterial Colonies

Single positive bacterial colonies were grown overnight and plasmid DNA was isolated according to the guidelines of the manufacturer (Qiagen). Plasmid DNA was sequenced using pTrcHis forward primer (GAGGTATATATTAATG-TATCG; SEQ ID NO.: 15).

Identification of a T Helper Cell Tumor Antigen by Screening a Tumor-Derived cDNA Expression Library Using the DANI Method To generate a tumor-derived cDNA expression library, mRNA was isolated from tumor cells and transcribed into double-stranded cDNA. Following digestion with frequently cutting restriction enzymes, the cDNA fragments of 30-300 bp in length were ligated into the bacterial expression vector system as described in the DANI method. *E. coli* XL-1 bacteria were transformed with the ligation mix, and pools of 60 bacterial colony forming units (cfu)/well were brought out in 96-well plates. Recombinant protein production was induced by addition of IPTG when the bacterial suspensions reached an optical density $OD_{j600}$ of 1. Four hours later, aliquots of the bacterial cultures were added to antigen-presenting cells (APC) which upon phagocytosis of bacteria present peptides derived from bacterial proteins—including recombinant tumor proteins—on MHC class II molecules. Following 24 hours of incubation, the bacteria-pulsed APC were co-cultured with the tumor-specific T cell clone C1-9 derived from the tumor patient for again 24 hours. Subsequently, the GM-CSF content in the cell culture supernatant was measured by ELISA.

A total of fifteen 96-well plates (equivalent to 15×96× 60=86400 single bacterial colonies or cDNA fragments) were screened.

Figure 12:
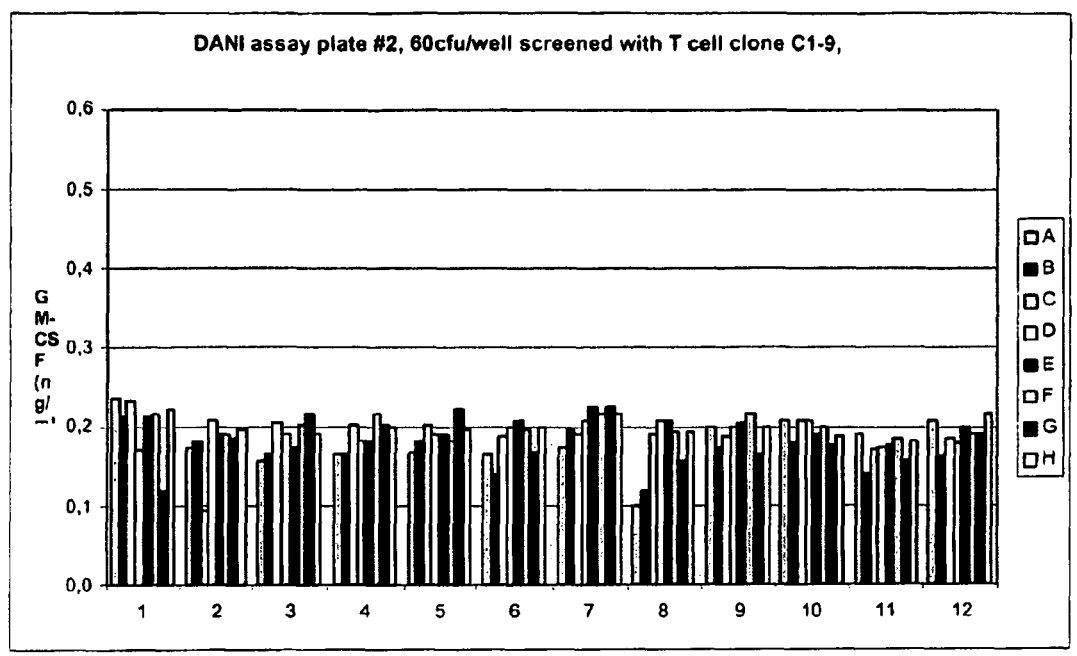

As exemplified in FIG. 12, no specific signal above background was detected in 14 of the 15 plates. In this example, the T cell clone did not recognize any of the proteins expressed in the bacterial pools of plate #2. Because T cells secrete cytokines only in response to antigen recognition, no specific signal above background was detected.

Of the fifteen 96-well plates screened, only the bacterial pool in well E3 of plate three stimulated the T cell clone.

Figure 13:
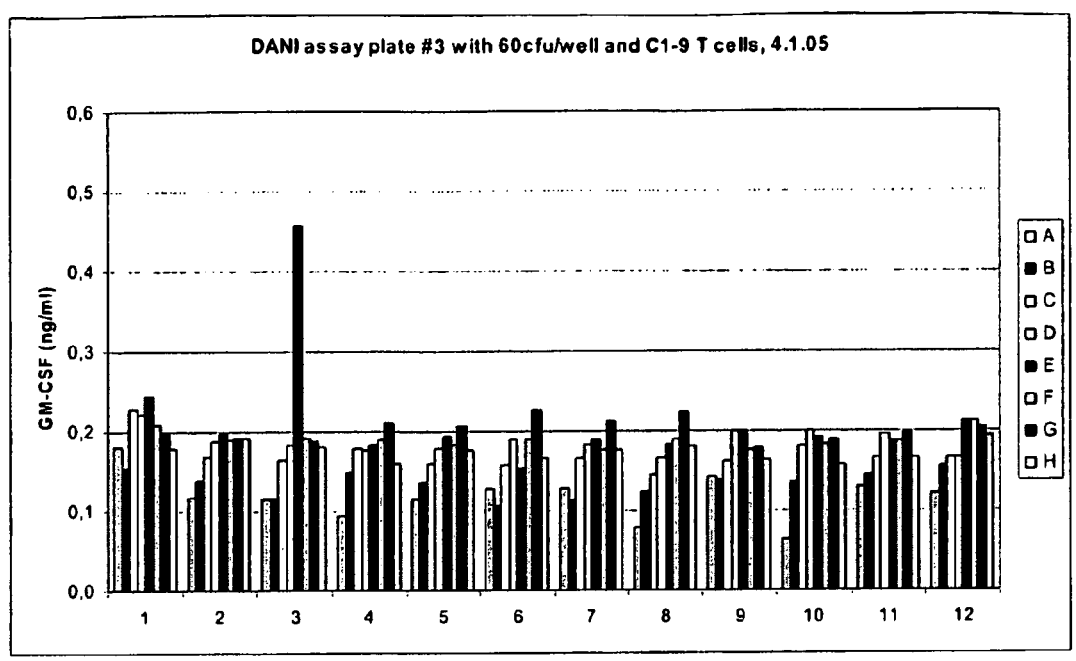

FIG. 13: The well E3 of plate #3 induced secretion of GM-CSF by the T cells. The bacterial pool from well E3 were plated on agar plates and single bacterial colonies tested for T cell recognition. Of 96 single colonies tested, six were recognized by the T cells. These six colonies were expanded, the plasmids extracted and the DNA inserts sequenced.

Figure 14:
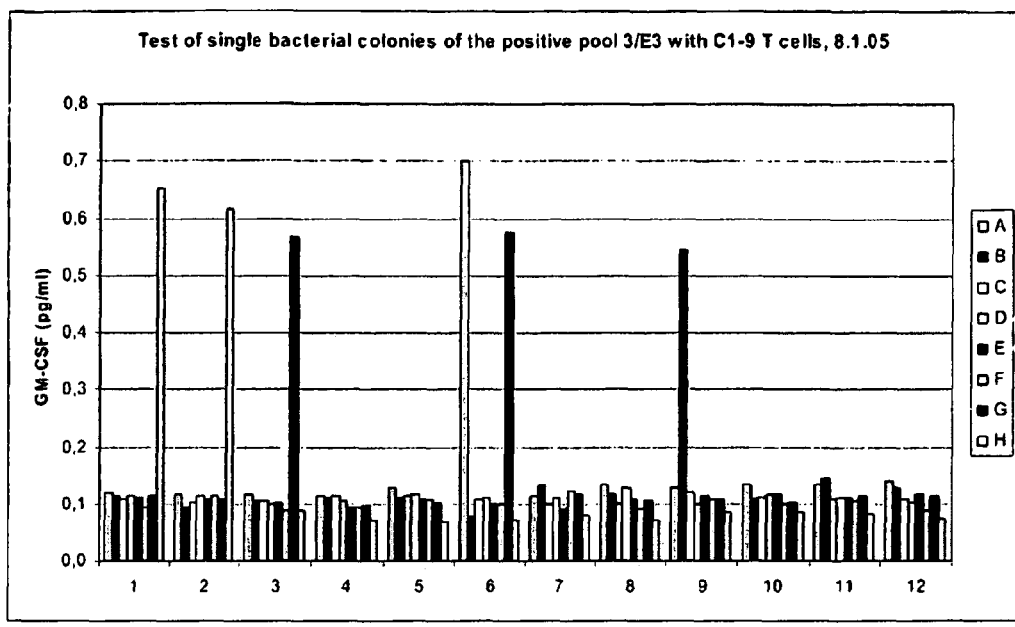

FIG. 14: Of 96 single bacterial colonies tested, six were recognized by the T cell clone C1-9. All plasmids extracted from the six bacterial colonies contained the same cDNA insert derived from a cellular gene expressed in the tumor. The epitope recognized by the T cell was mapped using the DEPI method, and subsequently verified using synthetic peptides. These results demonstrate that antigens recognized by T helper cells can be identified within complex cDNA libraries using the DANI method.

REFERENCES

Alderson, M. R., Bement, T., Day, C. H., Zhu, L., Molesh, D., Skeiky, Y. A., Coler, R., Lewinsohn, D. M., Reed, S. G. and Dillon, D. C. (2000) Expression cloning of an immunodominant family of *Mycobacterium tuberculosis* antigens using human CD4(+) T cells. *J Exp Med*, 191, 551-560.

Behrends U, Jandl T, Golbeck A, Lechner B, Muller-Weihrich S, Schmid 1, Till H, Berthold F, Voltz R, Mautner J M. (2002) Novel products of the HUD, HUC, NNP-1 and alpha-internexin genes identified by autologous antibody screening of a pediatric neuroblastoma library. *Int J Cancer*, 100, 669-677.

Davis, I. D., Chen, W., Jackson, H., Parente, P., Shackleton, M., Hopkins, W., Chen, Q., Dimopoulos, N., Luke, T., Murphy, R., Scott, A. M., Maraskovsky, E., McArthur, G., MacGregor, D., Sturrock, S., Tai, T. Y., Green, S., Cuthbertson, A., Maher, D., Miloradovic, L., Mitchell, S. V., Ritter, G., Jungbluth, A. A., Chen, Y. T., Gnjatic, S., Hoffman, E. W., Old, L. J. and Cebon, J. S. (2004) Recombinant NY-ESO-1 protein with ISCOMATRIX adjuvant induces broad integrated antibody and CD4(+) and CD8(+) T cell responses in humans. *Proc Natl Acad Sci USA*, 101, 10697-10702.

De Plaen E, Lurquin C, Lethe B, van der Bruggen P, Brichard V, Renauld J C, Coulie P, Van Pel A, Boon T. (1997) Identification of genes coding for tumor antigens recognized by cytolytic T lymphocytes. *Methods*, 12, 125-142.

Fujii, S., Senju, S., Chen, Y. Z., Ando, M., Matsushita, S. and Nishimura, Y. (1998) The CLIP-substituted invariant chain efficiently targets an antigenic peptide to HLA class II pathway in L cells. *Hum Immunol*, 59, 607-614.

Gorgievski-Hrisoho, M., Hinderer, W., Nebel-Schickel, H., Horn, J., Vornhagen, R., Sonneborn, H. H., Wolf, H. and Siegl, G. (1990) Serodiagnosis of infectious mononucleosis by using recombinant Epstein-Barr virus antigens and enzyme-linked immunosorbent assay technology. *J Clin Microbiol*, 28, 2305-2311.

(Halder T, Pawelec G, Kirkin A F, Zeuthen J, Meyer H E, Kun L, Kalbacher H. (1997) Isolation of novel HLA-DR restricted potential tumor-associated antigens from the melanoma cell line FM3. *Cancer Res*, 57, 3238-3244.

Hamanaka Y, Suchiro Y, Fukui M, Shikichi K, Imai K, Hinoda Y. (2003) Circulating anti-MUC1 IgG antibodies as a favorable prognostic factor for pancreatic cancer. *Int J Cancer*, 103, 97-100.

Horst, E., Wijngaard, P. L., Metzelaar, M., Bast, E. J. and Clevers, H. C. (1991) A method for cDNA cloning in COS cells irrespective of subcellular site of expression. *Nucleic Acids Res*, 19, 4556.

Jager, E., Nagata, Y., Gnjatic, S., Wada, H., Stockert, E., Karbach, J., Dunbar, P. R., Lee, S. Y., Jungbluth, A., Jager, D., Arand, M., Ritter, G., Cenndolo, V., Dupont, B., Chen, Y. T., Old, L. J. and Knuth, A. (2000) Monitoring CD8 T cell responses to NY-ESO-1: correlation of humoral and cellular immune responses. *Proc Natl Acad Sci USA*, 97, 4760-4765.

Kalams, S. A. and Walker, B. D. (1998) The critical need for CD4 help in maintaining effective cytotoxic T lymphocyte responses. *J Exp Med*, 188, 2199-2204.

Kieff, E. and Rickinson, A. B. (2001) Epstein-Barr virus and its replication. In: B. N. Fields, D. M. Knipe and P. M. Howley (Eds.) Fields Virology. Lippincott-Raven, Philadelphia, pp 2511-2573.

Kortt, A. A., Dolezal, O., Power, B. E. and Hudson, P. J. (2001) Dimeric and trimeric antibodies: high avidity scFvs for cancer targeting. *Biomol. Eng*, 18, 95-108.

Lemmel, C. and Stevanovic, S. (2003) The use of HPLC-MS in T-cell epitope identification. *Methods*, 29, 248-259.

Mautner J, Pich D, Nimmerjahn F, Milosevic S, Adhikary D, Christoph H, Witter K, Bornkamm G W, Hammerschmidt W, Behrends U. (2004) Epstein-Barr virus nuclear antigen 1 evades direct immune recognition by CD4+ T helper cells. *Eur J Immunol*, 34, 2500-2509.

McShane, M. P. and Longnecker, R. (2004) Cell-surface expression of a mutated Epstein-Barr virus glycoprotein B allows fusion independent of other viral proteins. *Proc Natl Acad Sci USA*, 101, 17474-17479.

Monach, P. A., Meredith, S. C., Siegel, C. T. and Schreiber, H. (1995) A unique tumor antigen produced by a single amino acid substitution. *Immunity*, 2, 45-59.

Moosmann, A., Khan, N., Cobbold, M., Zentz, C., Delecluse, H. J., Hollweck, G., Hislop, A. D., Blake, N. W., Croom-Carter, D., Wollenberg, B., Moss, P. A., Zeidler, R., Rickinson, A. B. and Hammerschmidt, W. (2002) B cells immortalized by a mini-Epstein-Barr virus encoding a foreign antigen efficiently reactivate specific cytotoxic T cells. *Blood,* 100, 1755-1764.

Neuhierl, B., Feederle, R., Hammerschmidt, W. and Delecluse, H. J. (2002) Glycoprotein gp110 of Epstein-Barr virus determines viral tropism and efficiency of infection. *Proc Natl Acad Sci USA,* 99, 15036-15041.

Nimmerjahn, F., Kobelt, D., Steinkasserer, A., Menke, A., Hobom, G., Behrends, U., Bornkamm, G. W. and Mautner, J. (2003) Efficient generation and expansion of antigen-specific CD4+ T cells by recombinant influenza viruses. *Eur J Immunol,* 33, 3331-3341.

Pieper, R., Christian, R. E., Gonzales, M. I., Nislimura, M. I., Gupta, G., Senlage, R. E., Shabanowitz, J., Rosenberg, S. A., Hunt, D. F. and Topalian, S. L. (1999) Biochemical identification of a mutated human melanoma antigen recognized by CD4(+) T cells. *J Exp Med,* 189, 757-766.

Romero, P., Cerottini, J. C. and Speiser, D. E. (2004) Monitoring tumor antigen specific T-cell responses in cancer patients and phase I clinical trials of peptide-based vaccination. *Cancer Immunol Immunother,* 53, 249-255.

Sahara, H. and Shastri, N. (2003) Second class minors: molecular identification of the autosomal H46 histocompatibility locus as a peptide presented by major histocompatibility complex class II molecules. *J Exp Med,* 197, 375-385.

Sahin, U., Tureci, O. and Pfreundschuh, M. (1997) Serological identification of human tumor antigens. *Curr Opin Immunol,* 9, 709-716.

Sanderson, S., Frauwirth, K. and Shastri, N. (1995) Expression of endogenous peptide-major histocompatibility complex class II complexes derived from invariant chain-antigen fusion proteins. *Proc Natl Acad Sci USA,* 92, 7217-7221.

Speiser, D. E., Pittet, M. J., Rimoldi, D., Guillaume, P., Luescher, I. F., Lienard, D., Lejeune, F., Cerottini, J. C. and Romero, P. (2003) Evaluation of melanoma vaccines with molecularly defined antigens by ex vivo monitoring of tumor-specific T cells. *Semin Cancer Biol,* 13, 461-472.

van Bergen, J., Schoenberger, S. P., Verreck, F., Amons, R., Offringa, R. and Koning, F. (1997) Efficient loading of HLA-DR with a T helper epitope by genetic exchange of CLIP. *Proc Natl Acad Sci USA,* 94, 7499-7502.

van de Corput, L., Chaux, P., van der Meijden, E. D., De Plaen, E., Frederik Falkenburg, J. H. and van der Bruggen, P. (2005) A novel approach to identify antigens recognized by CD4 T cells using complement-opsonized bacteria expressing a cDNA library. *Leukemia,* 19, 279-285.

Wang, R. F., Wang, X., Atwood, A. C., Topalian, S. L. and Rosenberg, S. A. (1999a) Cloning genes encoding MHC class II-restricted antigens: mutated CDC27 as a tumor antigen. *Science,* 284, 1351-1354.

Wang, R. F., Wang, X. and Rosenberg, S. A. (1999b) Identification of a novel major histocompatibility complex class II-restricted tumor antigen resulting from a chromosomal rearrangement recognized by CD4(+) T cells. *J Exp Med,* 189, 1659-1668.

Wong, D. K., Dudley, D. D., Dohrenwend, P. B., Lauer, G. M., Chung, R. T., Thomas, D. L. and Walker, B. D. (2001) Detection of diverse hepatitis C virus (HCV)-specific cytotoxic T lymphocytes in peripheral blood of infected persons by screening for responses to all translated proteins of HCV. *J Virol,* 75, 1229-1235.

Zeng, G., Li, Y., El-Gamil, M., Sidney, J., Sette, A., Wang, R. F., Rosenberg, S. A. and Robbins, P. F. (2002) Generation of NY-ESO-1-specific CD4+ and CD8+ T cells by a single peptide with dual MHC class I and class II specificities: a new strategy for vaccine design. *Cancer Res,* 62, 3630-3635.

The invention claimed is:

1. Method of identifying CD4+ T cell antigens comprising the steps of:
   a) providing an antigen encoding nucleic acid from tissue of patients and obtaining antigenic fragments of said nucleic acid, wherein the fragments have a size ranging from about 25 to about 300 bp;
   b) expressing said fragments as a fusion protein comprising said fragment and a marker in a suitable host cell, wherein the marker is chloramphenicol acetyltransferase (CAT);
   c) contacting said fusion protein expressing cell with antigen presenting cells (APCs) and co-cultivating with antigen-specific CD4+ T cells;
   d) determining whether the CD4+ T cells are activated by said fusion protein expressing cells; and
   e) identifying the antigen fragments which activate the antigen-specific CD4+ T cells by sequence analysis.

2. The method of claim 1, wherein the fragments are obtained by cleaving the antigen encoding nucleic acid with one or more frequently cutting restriction enzymes or digested with nucleases.

3. The method of claim 2, wherein the restriction enzymes are selected from the group consisting of AciI, MnlI, BsaJI and CviJI.

4. The method of claim 2, wherein the nuclease is DNAseI.

5. The method of claim 1, wherein the fragments have a size ranging from about 40 to 200 bp.

6. The method of claim 1, 2 or 5, wherein said fragments are expressed as a fusion protein by introducing an expression vector, containing the nucleic acid sequence coding for the fragment and a marker, into the host cell.

7. The method of claim 6, wherein the expression vector is a plasmid.

8. The method of claim 1, wherein the host cell is selected from prokaryotic and lower eukaryotic cells.

9. The method of claim 8, wherein the lower eukaryotic cells are yeast cells.

10. The method of claim 8, wherein the prokaryotic cells are bacterial cells.

11. The method of claim 1, wherein the nucleic acid coding for the antigen is cDNA obtained by transcribing mRNA isolated from the antigen-expressing cells or tissue into cDNA.

12. The method of claim 1, wherein the APCs are selected from dendritic cells, macrophages and lymphocytes.

13. The method of claim 12, wherein the lymphocytes are from a lymphoblastoid cell line (LCL).

14. The method of claim 1, which further comprises expanding host cells recognized by antigen specific CD4+ T cells.

15. The method of claim 1, wherein the activation of said CD4+ T cells is measured by determining cytokine secretion or proliferation.

16. The method of claim 1, wherein the antigen-specific CD4+ T cells are isolated by in vitro stimulation of autologous stimulator cells, wherein the CD4+ T cells are isolated from peripheral blood, secondary lymphoid organs or tissue of patients.

17. The method of claim 16, wherein the secondary lymphoid organs are lymph nodes.

18. The method of claim 16, wherein the tissue of patients comprises tumor explants in the case of tumor patients or inflamed tissues in cases of autoimmunity or infection.

19. A method for selecting CD4+ T cell antigen variants comprising the steps of identifying a CD4+ T cell antigen by the method of claim 1 and selecting antigen variants with improved or diminished T cell stimulatory capacity compared to said CD4+ T cell antigen.

20. The method of claim 1, wherein the tissue of patients consists of tumor explants in the case of tumor patients or inflamed tissues in cases of autoimmunity or infection.

21. The method of claim 1, wherein the method provides for the identification of alternative open reading frames coding for CD4+ T cell antigens.

22. Method of identifying CD4+ T cell antigens comprising the steps of:
   a) providing an antigen encoding nucleic acid from tissue of patients and obtaining antigenic fragments of said nucleic acid, wherein the fragments have a size of about 90 bp;
   b) expressing one or more of said fragments as a fusion protein comprising said fragment and a marker in a suitable host cell, wherein the marker is CAT;
   c) contacting said fusion protein expressing cell with antigen presenting cells (APCs) and co-cultivating with antigen-specific CD4+ T cells;
   d) determining whether the CD4+ T cells are activated by said fusion protein expressing cells; and
   e) identifying the antigen fragments which activate the antigen-specific CD4+ T cells by sequence analysis.

* * * * *